(12) United States Patent
Weissleder et al.

(10) Patent No.: US 10,712,343 B2
(45) Date of Patent: Jul. 14, 2020

(54) MOLECULAR ANALYSIS OF TUMOR SAMPLES

(71) Applicant: The General Hospital Corporation, Boston, MA (US)

(72) Inventors: Ralph Weissleder, Peabody, MA (US); Hakho Lee, Acton, MA (US); Cesar Castro, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 15/401,806

(22) Filed: Jan. 9, 2017

(65) Prior Publication Data

US 2017/0122951 A1     May 4, 2017

Related U.S. Application Data

(63) Continuation of application No. 14/005,986, filed as application No. PCT/US2012/029976 on Mar. 21, 2012, now abandoned.

(60) Provisional application No. 61/515,065, filed on Aug. 4, 2011, provisional application No. 61/515,150, filed on Aug. 4, 2011, provisional application No. 61/466,135, filed on Mar. 22, 2011.

(51) Int. Cl.
| | |
|---|---|
| *G01N 33/574* | (2006.01) |
| *G01N 33/543* | (2006.01) |
| *G01N 33/58* | (2006.01) |
| *G01R 33/12* | (2006.01) |
| *G01N 24/08* | (2006.01) |
| *G01N 21/64* | (2006.01) |

(52) U.S. Cl.
CPC ....... *G01N 33/574* (2013.01); *G01N 21/6428* (2013.01); *G01N 24/088* (2013.01); *G01N 33/54326* (2013.01); *G01N 33/57484* (2013.01); *G01N 33/57492* (2013.01); *G01N 33/587* (2013.01); *G01R 33/1269* (2013.01); *G01N 2333/4725* (2013.01); *G01N 2333/485* (2013.01); *G01N 2333/70596* (2013.01); *G01N 2333/71* (2013.01); *G01N 2800/00* (2013.01); *G01N 2800/52* (2013.01)

(58) Field of Classification Search
CPC ............. G01N 2800/00; G01N 33/574; G01N 2800/52; G01N 33/54326; G01N 33/54346; G01N 33/587; G01R 33/1269
See application file for complete search history.

(56) References Cited

U.S. PATENT DOCUMENTS

| 4,110,681 | A | 8/1978 | Hofer et al. |
|---|---|---|---|
| 5,164,297 | A | 11/1992 | Josephson et al. |
| 5,166,620 | A | 11/1992 | Panosh |
| 5,423,315 | A | 6/1995 | Margosian |
| 6,069,534 | A | 5/2000 | Kobayashi |
| 6,365,362 | B1 | 2/2002 | Terstappen et al. |
| 7,198,920 | B1 | 4/2007 | Cheever |
| 8,836,334 | B2 | 9/2014 | Lee |
| 8,948,841 | B2 | 2/2015 | Martel |
| 2002/0036500 | A1 | 3/2002 | Uetake |
| 2002/0149369 | A1 | 10/2002 | Peck et al. |
| 2003/0104499 | A1 | 6/2003 | Pressman |
| 2003/0175947 | A1 | 9/2003 | Liu et al. |
| 2004/0014236 | A1 | 1/2004 | Albo et al. |
| 2007/0116602 | A1 | 5/2007 | Lee |
| 2007/0152669 | A1 | 7/2007 | Park et al. |
| 2007/0296413 | A1 | 12/2007 | Park |
| 2008/0113350 | A1 | 5/2008 | Terstappen |
| 2008/0305048 | A1 | 12/2008 | Josephson et al. |
| 2009/0045551 | A1 | 4/2009 | Weissleder et al. |
| 2009/0275057 | A1 | 5/2009 | Linke et al. |
| 2009/0146658 | A1 | 6/2009 | McDowell |
| 2011/0091987 | A1 | 4/2011 | Weissleder et al. |
| 2012/0129281 | A1 | 9/2012 | Weissleder et al. |
| 2014/0011217 | A1 | 1/2014 | Weissleder et al. |

FOREIGN PATENT DOCUMENTS

| RU | 2319743 C1 | 3/2008 |
|---|---|---|
| WO | 2007/147018 | 12/2007 |
| WO | 2008/075342 | 6/2008 |
| WO | WO 2009/026251 | 2/2009 |
| WO | 2009/045551 | 4/2009 |
| WO | 2012/129281 | 9/2012 |

OTHER PUBLICATIONS

Racila et al., PNAS, 1998, 95:4589-4594.*
Nakamori et al., Gastroenterology, 1994, 106(2): 353-361.*
Alper, "US NCI launches nanotechnology plan," J., Nat. Biotechnol., 22:1335-6 (2004).
Azuma H. et al., "Effect of combined therapy using balloon-occluded arterial infiision of cisplatin and hemodialysis with consurrent radiation for locally invasive bladder cancer," Am J Clin Oncol. 31(1):11-2Labstract, PubMed, PMID: 18376222 (2008).
Bast et al., "Translational crossroads for biomarkers," Clin. Cancer Res., 11:6103-8 (2005).
Betensky et al., "Influence of unrecognized molecular heterogeneity on randomized clinical trials," J. Clin. Oncol., 20:2495-9 (2002).
Bolton et al., "Assessment of automated image analysis of breast cancer tissue microarrays for epidemiologic studies," Cancer Epidemiol. Biomarkers Prev., 19:992-9 (2010).
Bozzetti et al., "Comparison Between Epidermal Growth Factor Receptor (EFGFR) Gene Expression in Primary Non-small Cell Lung Cancer (NSCLC) and in Fine-Needle Aspirates from Distant Metastic Sites," J. Thorac. Oncol., 3:18-22 (2008).

(Continued)

*Primary Examiner* — Hong Sang
(74) *Attorney, Agent, or Firm* — Fish & Richardson P.C.

(57) ABSTRACT

This invention relates to methods for diagnosing cancer, e.g., cancer of epithelial origin, by detecting the presence of tumor cells in a sample, based (at least in some embodiments) on the quantification of levels of four biomarkers, MUC1, EGFR, EpCAM, and HER2. In some embodiments, the methods are performed using diagnostic magnetic resonance (DMR), e.g., with a portable relaxometer or MR imager.

11 Claims, 13 Drawing Sheets

(56) References Cited

OTHER PUBLICATIONS

Brennan et al., "Antibody-based proteomics: fast-tracking molecular diagnostics in oncology," Nat. Rev. Cancer, 10:605-17 (2010).
Bruening et al., "Systematic review: comparative effectiveness of core-needle and open surgical biopsy to diagnose breast lesions," Ann. Intern. Med., 152:238-46 (2010).
Buermans et al., "Comprehensive gene-expression survey identifies wifl as a modulator of cardiomyocyte differentiation," PLoS One, 5(12):e15504, 12 pages (2010).
Creighton et al., "Residual breast cancers after conventional therapy display mesenchymal as well as tumor-initiating features," Proc. Natl. Acad. Sci. USA, 106:13820-5 (2009).
Cristofanilli et al., "Inflammatory breast cancer (IBC) and patterns of recurrence: understanding the biology of a unique disease," Cancer, 110:1436-44 (2007).
Cui et al., "Nanowire nanosensors for highly sensitive and selective detection of biological and chemical species," Science, 293:1289-1292 (2001).
D'Alfonso et al., "Accurately assessing her-2/neu status in needle core biopsies of breast cancer patients in the era of neoadjuvant therapy: emerging questions and considerations addressed," Am. J. Surg. Pathol., 34:575-81 (2010).
Durr et al., "Direct proteomic mapping of the lung microvascular endothelial cell surface in vivo and in cell culture," Nat. Biotechnol., 22:985-92 (2004).
Elghanian et al., "Selective colorimetric detection of polynucleotides based on the distance-dependent optical properties of gold nanoparticles," Science, 277:1078-1081 (1997).
Erez et al., "Cancer-Associated Fibroblasts Are Activated in Incipient Neoplasia to Orchestrate Tumor-Promoting Inflammation in an NF-kappaB-Dependent Manner," Cancer Cell, 17:135-47 (2010).
Farokhzad and Langer, "Impact of nanotechnology on drug delivery," ACS Nano, 3:16-20 (2009).
Ferrari, "Cancer nanotechnology: opportunities and challenges," Nat. Rev. Cancer, 5:161-71 (2005).
Gaster et al., "Matrix-insensitive protein assays push the limits of biosensors in medicine," Nat. Med., 15(11):1327-1332 (2009).
Giljohann and Mirkin, "Drivers of biodiagnostic development," Nature, 462:461-464 (2009) (Author Manuscript).
Hanahan and Weinberg, "The hallmarks of cancer," Cell, 100:57-70 (2000).
Hanash and Taguchi, "The grand challenge to decipher the cancer proteome," Nat. Rev. Cancer, 10:652-60 (2010).
Haun et al., "Bioorthogonal chemistry amplifies nanoparticle binding and enhances the sensitivity of cell detection," Nat. Nanotechnol., 5:660-665 (2010) (Author Manuscript).
Haun et al., "Micro-NMR for Rapid Molecular Analysis of Human Tumor Samples," Sci. Trans. Med., 3(71):71ra16 (2011)
Haun et al., "Molecular detection of biomarkers and cells using magnetic nanoparticles and diagnostic magnetic resonance," Methods Mol. Biol., 726:33-49 (2011).
Ho et al., "Heterogeneity of mucin gene expression in normal and neoplastic tissues," Canceer Res., 53:641-51 (1993).
International Preliminary Report on Patentability dated Apr. 15, 2010 in international application No. PCT/US2008/011541, 8 pages.
International Preliminary Report on Patentability in International Application No. PCT/US2012/029912, dated Sep. 24, 2013, 6 pages.
International Preliminary Report on Patentability in International Application No. PCT/US2012/029976, dated Oct. 3, 2013, 6 pages.
International Search Report and Written Opinion dated Dec. 18, 2008 in international application No. PCT/US2008/011541.
International Search Report and Written Opinion dated Jul. 19, 2012 in international application No. PCT/US2012/029976, 7 pgs.
International Search Report and Written Opinion dated Oct. 30, 2012 in International Application No. PCT/US2012/029912, 9 pgs.
Issadore et al., "Miniature magnetic resonance system for point-of-care diagnostics," Lab Chip, 11(13):2282-2287 (2011) (Author Manuscript).
Kaiser, "Medicine. Cancer's circulation problem," J., Science, 327:1072-4 (2010).
Kalluri and Weinberg, "The basics of epithelial-mesenchymal transition," J. Clin. Invest., 119:1420-8 (2009).
Khan et al., "Comprehensive axillary evaluation in neoadjuvant chemotherapy patients with ultrasonography and sentinel lymph node biopsy," Ann. Surg. Oncol., 12:697-704 (2005).
Komohara et al., "AM-3K, an anti-macrophage antibody, recognizes CD163, a molecule associated with an anti-inflammatory macrophage phenotype," J. Histochem. Cytochem., 54:763-71 (2006).
Lahat et al., "Vimentin is a novel anti-cancer therapeutic target; insights from in vitro and in vivo mice xenograft studies," PLoS One, 5:3e10105 (2010).
Lee et al., "Chip-NMR biosensor for detection and molecular analysis of cells," Nat. Med., 14:869-874 (2008) (Author Manuscript).
Lee et al., "Rapid detection and profiling of cancer cells in fine-needle aspirates," Proc. Natl. Acad. Sci. U.S.A., 106:12459-12464 (2009).
Lee et al., "Ultrasensitive detection of bacteria using core-shell nanoparticles and an NMR-filter system," Angew. Chem., 48:5657-5660 (2009) (Author Manuscript).
Leimgruber et al., "Behavior of endogenous tumor-associated macrophages assessed in vivo using a functionalized nanoparticle," Neoplasia, 11:459-68 (2009).
Lequin, "Enzyme immunoassay (EIA)/enzyme-linked immunosorbent assay (ELISA)," Clin. Chem., 51(12):2415-2418 (2005).
Liu and Wang, "Nanomedicine: Nanotechnology tackles tumours," Nat. Nanotechnol., 2:20-1 (2007).
Liu et al., "CMOS mini nuclear magnetic resonance system and its application to bimolecular sensing," IEEE ISSCC Digest Tech. Papers, 140-141 (2008).
Maheswaran et al., "Detection of mutations in EGFR in circulating lung-cancer cells," N. Engl. J. Med., 359:366-77 (2008).
Makris et al., "Quantitative changes in cytological molecular markers during primary medical treatment of breast cancer: a pilot study," Breast Cancer Res. Treat., 53:51-9 (1999).
Mitchell, "Proteomics retrenches," Nat. Biotechnol., 28:665-670 (2010).
Mueller and van Sonnenberg, "Interventional radiology in the chest and abdomen," N. Engl. J. Med., 322:1364-74 (1990).
Nagrath et al., "Isolation of rare circulating tumour cells in cancer patients by microchip technology," Nature, 450:1235-9 (2007) (Author Manuscript).
Niemeyer et al., "Immuno-PCR: high sensitivity detection of proteins by nucleic acid amplification," Trends in Biotech., 23(4):208-216 (2005).
Pierga et al., "Circulating tumor cell detection predicts early metastatic relapse after neoadjuvant chemotherapy in large operable and locally advanced breast cancer in a phase II randomized trial," Clin. Cancer Res., 14:7004-10 (2008).
Piyathilake et al., "The Expression of Ep-CAM (17-1A) in Squamous Cell Cancers of the Lung," Human Pathology, 31(4):482-487 (2000).
Ramaswamy et al., "A molecular signature of metastasis in primary solid tumors," Nat. Genet., 33:49-54 (2003).
Rosenthal et al., "Biocompatible quantum dots for biological applications," Chem Biol., 18:10-24 (2011).
Roth et al., "B7-H3 ligand expression by prostate cancer: a novel marker of prognosis and potential target for therapy," Cancer Res., 67:7893-900 (2007).
Saadi et al., "Stromal genes discriminate preinvasive from invasive disease, predict outcome, and highlight inflammatory pathways in digestive cancers," Proc. Natl. Acad. Sci. USA, 107:2177-82 (2010).
Sequist et al., "The CTC-chip: an exciting new tool to detect circulating tumor cells in lung cancer patients," J. Thorac. Oncol., 4:281-3 (2009).
Shaffer et al., "Circulating tumor cell analysis in patients with progressive castration-resistant prostate cancer," Clin. Cancer Research, 13(7):2023-2029 (2007).
Sheiman et al., "Possible causes of inconclusive results on CT-guided thoracic and abdominal core biopsies," Am. J. Roentgenol., 170:1603-7 (1998).

(56) References Cited

OTHER PUBLICATIONS

Shi et al., "Quantum dots-based multiplexed immunohistochemistry of protein expression in human prostate cancer cells," Eur. J. Histochem., 52(2):127-134 (2008).
Spencer et al., "Non-genetic origins of cell-to-cell variability in TRAIL-induced apoptosis," Nature, 459:428-32 (2009) (Author Manuscript).
Stott et al., "Isolation and characterization of circulating tumor cells from patients with localized and metastatic prostate cancer," Sci. Transl. Med., 2:25ra23 (2010) (Author Manuscript).
Sun et al., "A microfluidic platform for systems pathology: multiparameter single-cell signaling measurements of clinical brain tumor specimens," Cancer Res., 70:6128-38 (2010).
Sun et al., "CMOS RF Biosensor Utilizing Nuclear Magnetic Resonance," IEEE J. Solid-State Circuits, 44:1629-1643 (2009).
Sun et al., "Palm NMR and one-chip NMR," IEEE ISSCC Digest Tech. Papers, 488-489 (2010).
Swirski et al., "Identification of splenic reservoir monocytes and their deployment to inflammatory sites," Science, 325:612 (2009) (Author Manuscript).
Tan et al., "Biomarker-driven early clinical trials in oncology: a paradigm shift in drug development," Cancer J., 15:406-20 (2009).
Taylor et al., "A systems approach to model metastatic progression," Cancer Res., 66:5537-9 (2006).
Thaxton et al., "Nanoparticle-based bio-barcode assay redefines "undetectable" PSA and biochemical recurrence after radical prostatectomy," PNAS, 106(44):18437-18442 (2009).
Tsao et al, "Erlotinib in lung cancer—molecular and clinical predictors of outcome," N. Engl. J. Med., 353:133-44 (2005).
U.S. Final Office Action in U.S. Appl. No. 12/681,303, dated Aug. 27, 2014, 9 pages.
U.S. Final Office Action in U.S. Appl. No. 12/681,303, dated May 30, 2012, 9 pages.
U.S. Non-Final Office Action in U.S. Appl. No. 12/681,303, dated Feb. 6, 2012, 8 pages.
U.S. Non-Final Office Action in U.S. Appl. No. 12/681,303, dated May 13, 2014, 9 pages.
Vogel et al., "Efficacy and safety of trastuzumab as a single agent in first-line treatment of HER2-overexpressing metastatic breast cancer," J. clin. Oncol., 20:719-26 (2002).
Von Hoff et al., "Pilot study using molecular profiling of patients' tumors to find potential targets and select treatments for their refractory cancers," J. Clin. Oncol., 28:4877-83 (2010).
Wang et al., "Colorimetric multiplexed immunoassay for sequential detection of tumor markers," Biosens. Bioelectron., 25(2):532-536 (2009).
Wang et al., "In situ amplified chemiluminescent detection of DNA and immunoassay of IgG using special-shaped gold nanoparticles as label," Clin. Chem., 52:1958-1961 (2006).
Wang et al., "Ultrasensitive electrical biosensing of proteins and DNA: carbon-nanotube derived amplification of the recognition and transduction events," J. Am. Chem. Sco., 126:3010-3011 (2004).
Wildgrubert et al., "Monocyte subset dynamics in human atherosclerosis can be profiled with magnetic nano-sensors," PLoS One, 4:e5663, 9 pages (2009).
Wilson et al., "Detection of myocardial injury in patients with unstable angina using a novel nanoparticle cardiac troponin I assay: observations from the PROTECT-TIMI 30 Trial," Am Heart J., 158:386-391 (2009).

Xing et al., "Bioconjugated quantum dots for multiplexed and quantitative immunohistochemistry," Nature Protocols, 2:1152-1165 (2007).
Zellweger et al., "Expression patterns of potential therapeutic targets in prostate cancer," Int. J. Cancer, 113:619-628 (2005).
Barna et al., "Structure Elucidation of the Teicoplanin Antibodies," J. Am. Chem. Soc., 6:4895-4902 (1984).
Bu, et al., "A new masking technology for deep glass etching and its microfluidic application," Sensors and Actuators A, 115(2-3):476-482 (2004).
Cheng et al., "Nanotechnologies for biomolecular detection and medical diagnostics," Curr. Opin. Chem. Biol., 10:11-19 (2006).
Chin et al., "Lab-on-a-chip devices for global health: past studies and future opportunities," Lab Chip, 7:41-57 (2007).
Danieli et al., "Small magnets for portable NMR spectrometers," Angew. Chem., 49:4113-4135 (2010).
El-Ali, et al., "Cells on chips," Nature, 442:403-411 (2006).
Gillis et al., "On $T_2$-shortening by strongly magnetized spheres: a partial refocusing model," Magn. Reson. Med., 47:257-263 (2002).
Grimm et al., "Novel nanosensors for rapid analysis of telomerase activity," Cancer Research, 64:639-643 (2004).
Gueron, "Nuclear Relaxation in Macromolecules by Paramagnetic Ions: A Novel Mechanism," J. Magn. Reson., 19:58-66 (1975).
Issadore et al., "Self-assembled magnetic filter for highly efficient immunomagnetic separation," Lab Chip, 11:147-51 (2010) (Author Manuscript).
Josephson et al., "High-efficiency intracellular magnetic labeling with novel superparamagnetic-Tat peptide conjugates," Bioconjugate Chem., 10:186-191 (1999).
Josephson et al., "Magnetic Nanosensors for the Detection of Oligonucleotide Sequences," Angew. Chem., 113:3304-3306 (2001).
Keeler et al., "Reducing the Global Burden of Tuberculosis: The Contribution of Improved Diagnostics," Nature, 444:49-57 (2006).
Liu et al., "Passive mixing in a three-dimensional serpentine microchannel," 2000, J Microelectromechanical Systems, 9(2):190-197 (2000).
Melin and Quake, "Microfluidic large-scale integration: the evolution of design rules for biological automation," Annu. Rev. Biomol. Struct., 36:213-231 (2007).
Moresi et al., "Miniature permanent magnet for table-top NMR," Concepts in Magnetic Resonance Part B: Magnetic Resonance Engineering, 19B(1):35-43 (2003).
Perez et al., "Magnetic relaxation switches capable of sensing molecular interactions," Nat. Biotechnol., 20:816-820 (2002).
Trumbull, et al., "Integrating microfabricated fluidic systems and NMR spectroscopy," IEEE Trans Biomed Eng., 47(1):3-7 (2000).
Tsourkas et al., "Magnetic Relaxation Switch Immunosensors Detect Enantiomeric Impurities," Angew. Chem., 116:2449-2453 (2004).
Urdea et al., "Requirements for high impact diagnostics in the developing world," Nature, 444:73-79 (2006).
U.S. Office Action in U.S. Appl. No. 14/006,389, dated Mar. 1, 2017.
Wensink et al., "Measuring reaction kinetics in a lab-on-a-chip by microcoil NMR," Lab Chip, 5:280-284 (2005).
Xia, et al., "Chaotic micromixers using two-layer crossing channels to exhibit fast mixing at low Reynolds numbers," Lab. Chip, 5:748-755 (2005).
Yager et al., "Point-of-care diagnostics for global health," Annu Rev. Biomed Eng., 10:107-144 (2008).
Zhao et al., "Differential conjugation of tat peptide to superparamagnetic nanoparticles and its effect on cellular uptake," Bioconjugate Chem., 13:840-844 (2002).

* cited by examiner

| Tool or technique | Read out | Detection limit | In clinical use? | Drawbacks | Refs |
|---|---|---|---|---|---|
| Colorimetry | Visual | 150 pM | Yes | stringent processing needs; timing of reactions critical; sensitive to pH, charge, reducing & chelating agents; laborious | Science 277, 1078-1081 1997; Elsevier Bioscience, 2009 Oct 15;25(2):532-6 |
| Carbon nanotubes | Electrical | 100pM | No | relies on charge-based interactions, depends on pH or ionic strength | J. Am. Chem. Soc 128 (5), 2011-2006 |
| Chemi-luminescence | Luminescence | 100pM | Yes | small linear dynamic range; incompatible with multiplexing | Clin. Chem. 52, 1985-1993, 2006 |
| ELISA | Luminescence | 1-10pM | Yes | highly skilled personnel; laborious; costly; usually singleplex; newer multiplex ELISAs have very high fixed costs | Clin. Chem. 51(12) 2415-22, 2005 |
| Quantum Dots | Fluorescence | 500fM | No | in vivo toxicity; multivalency; non-specific binding and/or protein adsorption; large functional probe size | Chemistry & Biology 18, January 28, 2011 |
| Silicon nanowires | Electrical | fM | No | small linear dynamic range; relies on charge-based interactions depends on pH or ionic strength; | Science 293, 1289-1292 (2001) |
| Bio-barcodes | Scanometric / Light scattering | 30aM | Yes | scanometric detection saturates at higher signals which limits multiplexing; | Anal. Bioan. Journal 138, 1889-91, 2009; PNAS 106 (44):18437-42, 2009 |
| Immuno-PCR | Fluorescence | 30aM | Yes | Limited multiplexing; not point of care; high fixed costs; highly trained technicians needed; laborious | Trends in Biotech Vol 23 No.4 April 2005 |
| LC-Mass Spec | Mass-to-charge | femtomoles | Yes | semi-quantitative; expensive; time consuming; laborious | Nat Biotechnol 28, 695-879, 2010 |
| Giant magnetoresistance chip | Electrical | not reported | No | unproven in human cancer specimens; still experimental; relies on immuno-specific sandwiching (steric hindrance limitations) | Nat Med. 2009 Nov 15 (11):1327-32 |
| Aptamer-based arrays | Fluorescence | not reported | No | laborious; need for high skilled tech; bioinformatics heavy; unproven in cancer | PLoS ONE 5(12), e15004, 2010 |
| Microfluidic image cytometry | Fluorescence | not reported | No | laborious; time consuming; bioinformatics and statistics heavy (needs to be robustly analyzed) | Cancer Res. 70(19) August 1, 2010 |

FIG. 10A

| Tool or technique | Read out | In clinical use? | Drawbacks | Refs |
|---|---|---|---|---|
| Veridex | Fluorescence | Yes | semi-automated; limited to EpCAM+, CK+, DAPI+ and CD45- cells; misses EpCAM negative or low level expression; interference from Doxorubicin up to 7 days post-administration (assay can't be used reliably during this period) | Clin Cancer Research 13, 7: 2023-2029 (2007) |
| Flow cytometry | Fluorescence | Yes | large sample consumption when multiplexing (not appropriate for specimen-limited scenarios) | many |
| Immunohistochemistry (IHC) | Colorimetric | Yes | large sample consumption when multiplexing (not appropriate for specimen-limited scenarios); non-specific labeling a common concern | many |
| IHC with spectrum dots | Fluorescence | No | multiplexing results can take up to 3 days; methods for CD-isolation (CD-Ab interaction, tissue specimen preparation, multicolor QD dosing, image processing and data quantitation), high cost of reagents, increase of time and labors, and chemical/ non-specific binding of acceptor probes | Nat Biotechnol. 2004 Aug; 22(8): 969-976; Nat Protoc. 2, 1152-1165 (2007) |

FIG. 10B

MOLECULAR ANALYSIS OF TUMOR SAMPLES

CLAIM OF PRIORITY

This application is a continuation of U.S. patent application Ser. No. 14/005,986, with a § 371 filing date of Nov. 27, 2013, which is a U.S. National Phase Application under 35 U.S.C. § 371 of International Patent Application No. PCT/US2012/029976, filed on Mar. 21, 2012, which claims the benefit of U.S. Provisional Patent Application Ser. Nos. 61/515,065, filed on Aug. 4, 2011; 61/515,150, filed on Aug. 4, 2011; and 61/466,135, filed on Mar. 22, 2011. The entire contents of the foregoing are hereby incorporated by reference.

FEDERALLY SPONSORED RESEARCH OR DEVELOPMENT

This invention was made with Government support under Grant Nos. RO1 EB004626, RO1 EB010011, U54 CA119349, UO1 HL080731, P50 CA127003, T32 CA079443, and F32 CA144139 awarded by the National Institutes of Health. The Government has certain rights in the invention.

TECHNICAL FIELD

This invention relates to methods for diagnosing cancer by detecting the presence of tumor cells in a patient sample, based (at least in some embodiments) on the detection of four biomarkers: MUC1, EGFR, EpCAM, and HER2.

BACKGROUND

Primary and metastatic solid tumors comprise cancer cells, host cells such as endothelial cells and fibroblasts, and inflammatory immune cells. Yet, although individual cancer cells may exhibit a stable signature of protein marker expression (S. Ramaswamy et al., Nat. Genet. 33, 49 (2003); B. S. Taylor et al., Cancer Res. 66, 5537 (2006)), tumors in general are highly adaptive and heterogeneous (S. Maheswaran et al., N. Engl. J. Med. 359, 366 (2008); D. Hanahan and R. A. Weinberg, Cell 100, 57 (2000)) and thus may respond differently to therapeutics based on stochastic differences in protein expression across the cancer cell population (S. L. Spencer et al., Nature 459, 428 (2009)). It is therefore becoming clear that molecular diagnosis using cancer cells will yield critical information for classifying tumors, stratifying patients for molecular targeted therapies and for assessing treatment efficacy (D. D. Von Hoff et al., J. Clin. Oncol. 28, 4877 (2010)). Expanding knowledge of the proteome in clinically harvested cancer cells may also yield new information about tumor biology (D. J. Brennan et al., Nat. Rev. Cancer 10, 605 (2010)).

Within a clinical setting, cancer cells from primary tumors are typically obtained through image-guided intervention or open surgical procedures (W. Bruening et al., Ann. Intern. Med. 152, 238 (2010)). Percutaneous biopsy is a well-established clinical procedure that yields cells for cytology using 22-gauge (22 G) fine-needle aspirates, and small tissue fragments for histology by core biopsies using 16 G to 19 G needles. Samples are commonly processed using conventional histological stains before immunohistochemical evaluation if sufficient tissue remains (tissue sections contain billions of cells). However, immunohistochemical evaluation is only semiquantitative, time-consuming, and technically challenging.

SUMMARY

Described herein are methods for multiplexed analysis of protein expression in cancer cells. In some embodiments, the methods are practiced using a point-of-care molecular diagnostic system for rapid, quantitative, and multiplexed analysis of protein expression in cancer cells, e.g., cells obtained by fine-needle aspirates of patients' tumors, for real-time analysis within a clinical setting.

Thus, in one aspect, the invention provides methods for diagnosing a tumor in a subject. The methods include obtaining a sample from the subject; detecting levels of MUC-1, HER2, EGFR, and EpCAM in the sample; and comparing the levels of MUC-1, HER2, EGFR, and EpCAM in the sample to reference levels; and diagnosing cancer in a subject who has levels of MUC-1, HER2, EGFR, and EpCAM above the reference levels.

In a further aspect, the invention features methods for detecting the presence of tumor cells in a sample. The methods include detecting levels of MUC-1, HER2, EGFR, and EpCAM in the sample; and comparing the levels of MUC-1, HER2, EGFR, and EpCAM in the sample to reference levels; wherein the presence in a sample of levels of MUC-1, HER2, EGFR, and EpCAM above the reference levels indicates the presence of tumor cells in the sample.

In some embodiments, detecting levels of MUC-1, HER2, EGFR, and EpCAM in the sample comprises contacting the sample with antibodies or antigen-binding fragments thereof that bind to MUC-1, HER2, EGFR, and EpCAM. In some embodiments, the antibodies are labeled, e.g., with magnetic nanoparticles, e.g., MIONs, e.g., CLIOs.

In some embodiments, a single undivided sample is contacted with a mixture of antibodies, or antigen-binding fragments thereof, that bind to MUC-1, HER2, EGFR, and EpCAM, substantially simultaneously.

In some embodiments, the sample is subdivided into at least four subparts, and each antibody, or antigen-binding fragment thereof, that binds to MUC-1, HER2, EGFR, or EpCAM is contacted with a single subpart.

In some embodiments, the levels of each of the biomarkers MUC-1, HER2, EGFR, and EpCAM are weighted. In some embodiments, a quad biomarker value for a sample is determined using the following weighted equation:

$$\text{Quad Biomarker Value} = 4.90 * \text{Muc1} + 4.55 * \text{EGFR} + 1.54 \text{Her2} + 4.79 \text{EpCAM}$$

In some embodiments, the levels of MUC-1, HER2, EGFR, and EpCAM are detected using diagnostic magnetic resonance (DMR), e.g., using a portable relaxometer or MR imager; direct magnetic detection (e.g., using mass spectrometry or nanoparticle-based bio barcoding methods); optical detection methods (e.g., flow cytometry, fluorescence detection, e.g., with quantum dots); or electric measurements (e.g., using nanowires, or giant magnetosensor chips).

In some embodiments, the sample comprises blood or a subfraction thereof, e.g., buffy coat. In some embodiments, the sample comprises a biopsy sample, e.g., a fine needle aspirate (FNA), endoscopic biopsy, or core needle biopsy. In some embodiments, the sample comprises cells from the pancreas, lung, breast, prostate, kidney, stomach, esophagus, bladder, endometrial, cervix, biliary, thyroid ovary or colon of the subject.

In some embodiments, the tumor is a pancreas, lung, breast, prostate, kidney, stomach, esophagus, bladder, endometrial, cervix, biliary, thyroid ovary or colon tumor.

In another aspect, the invention provides kits including reagents for detection of tumor cells, wherein the reagents comprise a panel of antigen-binding reagents consisting of: antibodies or antigen-binding fragments thereof that bind to MUC1, antibodies or antigen-binding fragments thereof that bind to EGFR, antibodies or antigen-binding fragments thereof that bind to HER2, and antibodies or antigen-binding fragments thereof that bind to EpCAM.

In some embodiments, the antibodies or antigen-binding fragments thereof are linked to superparamagnetic nanoparticles, e.g., MIONs, e.g., CLIOs. In some embodiments, the antibodies or antigen-binding fragments thereof are linked to superparamagnetic nanoparticles via trans-cyclooctene (TCO)/tetrazine (Tz) chemistry.

In an additional aspect, the invention provides methods for isolating tumor cells from a sample. The methods include providing a sample comprising or suspected of comprising tumor cells; contacting the sample with:

antibodies or antigen-binding fragments thereof that bind to MUC1, antibodies or antigen-binding fragments thereof that bind to EGFR, antibodies or antigen-binding fragments thereof that bind to HER2, and antibodies or antigen-binding fragments thereof that bind to EpCAM; under conditions sufficient for the antibodies or antigen-binding fragments thereof to bind to tumor cells in the sample; and removing the antibodies or antigen-binding fragments thereof that are bound to tumor cells from the sample, thereby isolating tumor cells from the sample.

In some embodiments, the antibodies or antigen-binding fragments thereof are linked to superparamagnetic nanoparticles, and the antibodies or antigen-binding fragments thereof that are bound to tumor cells are removed from the sample by application of a magnetic field to the sample.

In some embodiments, the sample comprises blood from a subject. In some embodiments, the method further comprises returning the blood to the subject after removal of the tumor cells.

The terms "quad biomarkers" or "the biomarkers" as used herein refers to MUC1, EpCAM, HER2, and EGFR.

An "epithelial cancer," as used herein is defined by the ICD-O (International Classification of Diseases—Oncology) code (revision 3), section (8010-8790), and can include tumors of the pancreas, lung, breast, prostate, kidney, ovary or colon.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 10A-B are tables presenting various methods of detection.

DETAILED DESCRIPTION

Figure 1:
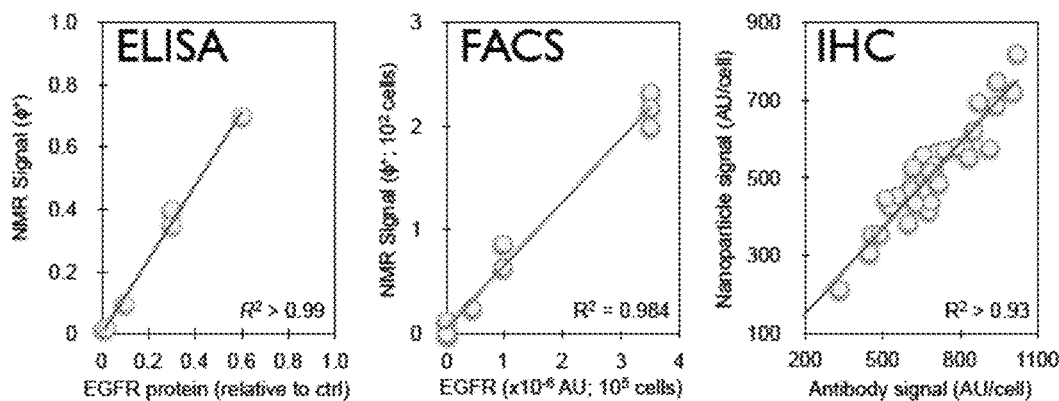
FIG. 1 is a set of three line graphs demonstrating validation of NMR measurements. The plots show the correlation of EGFR measurements obtained by μNMR versus ELISA, FACS or immunohistochemistry (IHC) in clinical samples where sufficient cells were available for conventional proteomic techniques (typically $10^{5-6}$ for ELISA and FACS versus $10^2$ for DMR). Note the excellent correlation coefficients for the different methods.

While results from several studies have indicated that molecular profiling of solid tumors improves treatment stratification (M. S. Tsao et al., N. Engl. J. Med. 353, 133 (2005)) and efficacy monitoring (D. S. Tan et al., Cancer J. 15, 406 (2009)), failure to detect molecular heterogeneity in cancer patients can lead to underpowered clinical trials (R. A. Betensky et al., J Clin Oncol 20, 2495 (2002)). However, the availability of serial tumor tissue to make such decisions during treatment is often limited since core biopsies carry procedural risks, are time consuming, and are costly. Moreover, biopsies often yield small amounts of tissue (about several $mm^3$), which allow for only limited analyses. Conventional methods for molecular profiling (immunohistochemistry, flow cytometry or proteomic techniques) often require considerable cell and/or tissue quantities, both of which are not easily obtained via FNA. These caveats have fueled an intense interest in developing more sensitive technologies for enabling broader profiling of tissue in limited clinical specimens. Recent advances in nanotechnology and device miniaturization have made sophisticated molecular and cellular analyses of scant tumor samples possible, albeit often under well-controlled experimental conditions (H. Lee et al., Nat. Med. 14, 869 (2008); Y. Liu and H. Wang, Nat. Nanotechnol. 2, 20 (2007); D. A. Giljohann and C. A. Mirkin, Nature 462, 461 (2009)). Yet, despite the development of various platforms through the NCI's Cancer Nanotechnology Initiative (J. Alper, Nat. Biotechnol. 22, 1335 (2004); M. Ferrari, Nat. Rev. Cancer 5, 161 (2005); O. C. Farokhzad and R. Langer, ACS Nano 3, 16 (2009)), only a few of these have advanced into clinical feasibility trials (S. Maheswaran et al., N. Engl. J. Med. 359, 366 (2008); S. Nagrath et al., Nature 450, 1235 (2007); L. V. Sequist et al., J. Thorac. Oncol. 4, 281 (2009); S. L. Stott et al., Sci. Transl. Med. 2, 25ra23 (2010); C. S. Thaxton et al., Proc. Natl. Acad. Sci. U.S.A. 106, 18437 (2009); J. Sun et al., Cancer Res. 70, 6128 (2010)).

The present study revealed several unexpected findings. First, considerable expression heterogeneity was observed for all biomarkers across the sample populations. For example, EpCAM, the current marker of choice to define CTCs, was only highly expressed in ~60% of cancers and completely absent in ~20%. Second, significant expression heterogeneity was observed along identical and distal biopsy sites within a given tumor lesion. These findings have important implications for both molecular diagnostics and therapeutic drug targeting. Third, time courses were obtained on protein viability that demonstrated rapid decay, informing the need for prompt proteomic and other molecular measurements of human samples. Finally, molecular profiling based on multi-marker diagnostics in a point-of-care setting can have higher diagnostic accuracies when compared to state-of-the-art conventional pathology.

Of the individual biomarkers investigated, MUC-1, HER2, EGFR, and EpCAM provided the highest diagnostic accuracy. Combining these four markers established correct diagnoses in 48 of the 50 patients in the initial cohort, and in all 20 patients in the independent test set. This accuracy was superior to conventional clinical analysis. In the two misclassified cases, core biopsy showed significant inflammation and an absence of cancer cells. In some embodiments, one or more additional markers that define monocyte, macrophage, and fibroblast populations more accurately (e.g., CD163, CD14, CD16, CD33, and 5B5) are also detected, and used to characterize the inflammatory and stromal components of FNAs, and increase specificity (Y. Komohara et al., J. Histochem. Cytochem. 54, 763 (2006); A. Leimgruber et al., Neoplasia 11, 459 (2009); F. K. Swirski et al., Science 325, 612 (2009); M. Wildgruber et al., PLoS One 4, e5663 (2009)). The current study was specifically designed to include a range of intra-abdominal tumor types so as to simulate the typical clinical referral pattern seen at an interventional service. It is noteworthy that the three and four marker combinations were found to offer similar predictive accuracies, both being superior to EpCAM alone and to conventional cytopathology. In order to be specific for particular cancer subsets, additional protein markers can be detected that recognize (and thus can be used to diagnose) specific epithelial (e.g., prostate or lung cancer) or non-epithelial cancers (e.g., melanoma, sarcoma, lymphoma). The present markers can be used in methods of detecting the presence of cancer, e.g., epithelial cancer, or glioma.

With respect to protein stability, all of the cancer markers displayed relatively short half-lives once harvested. To date, very limited information has been available on the half-life of protein expression levels in aspirated cancer cells, and marker degradation may be one of the reasons for the lower detection sensitivities reported in some studies. Proteomic studies of freshly harvested nonmalignant cells have demonstrated that up to 40% of protein markers are differentially expressed when in vivo to in vitro conditions are compared (E. Durr et al., Nat. Biotechnol. 22, 985 (2004)). Within the first hour after harvesting, a mean decrease of ~100% in marker expression was observed across the different markers studied (FIG. 9F) in saline or whole blood samples. The magnitude of this effect was unexpected and indicates that samples either require rapid analysis (e.g., within minutes) or preservation using methods, such as those described herein, to maintain molecular expression integrity.

Thus, the methods described herein include the detection of multiple markers in the sample within 30 minutes of harvesting the sample, e.g., within about 20 minutes, within about 15 minutes, within about 10 minutes, or within about 5 minutes. "Harvesting" refers to any method suitable for obtaining a sample from a subject, e.g., blood draw, tissue biopsy, core needle, lavage, or fine needle aspirate.

Described herein are methods for diagnosing or detecting the presence of a cancer in a subject. The methods include obtaining a sample from a subject, and evaluating the presence and/or level of MUC-1, HER2, EGFR, and EpCAM in the sample, and comparing the presence and/or level with one or more references, e.g., a control reference that represents a normal level of MUC-1, HER2, EGFR, and EpCAM, e.g., a level in an unaffected subject, and/or a disease reference that represents a level of the proteins associated with MUC-1, HER2, EGFR, and EpCAM, e.g., a level in a subject having cancer. In some embodiments, the methods include determining a value, e.g., a normalized expression value, for each of the biomarkers (MUC-1, HER2, EGFR, and EpCAM), and calculating a test score from the sum of each of the levels. This score can then be compared to a reference score, wherein the presence of a test score above (e.g., equal to or above, or simply above) the reference score indicates the presence of cancer in the subject.

In some embodiments, the quad biomarker value for a sample is determined using the following weighted equation:

Quad Biomarker Value=4.90*Muc1+4.55*EGFR+ 1.54Her2+4.79EpCAM

The level of each of the biomarkers is determined and normalized, e.g., using DMR as described herein. In some embodiments, a quad biomarker value of 1.6 or greater indicates that the sample (or lesion) is malignant. In some embodiments, the threshold quad biomarker value is 1, 1.2. 1.3, 1.4, 1.5, 1.6, 1.7, 1.8, 1.9, or 2.0, and a level above the threshold indicates the presence of cancerous cells in the sample.

In some embodiments, the presence and/or level of MUC-1, HER2, EGFR, and EpCAM is comparable to the presence and/or level of the protein(s) in the disease reference, and the subject has one or more symptoms associated with cancer, then the subject has cancer. In some embodiments, the subject has no overt signs or symptoms of cancer, but the presence and/or level of MUC-1, HER2, EGFR, and EpCAM is comparable to the presence and/or level of the protein(s) in the disease reference, then the subject has cancer.

In some embodiments, once it has been determined that a person has cancer, then a treatment for cancer, e.g., as known in the art or as described herein, can be administered.

The methods also can be used to monitor a patient, e.g., to determine whether a treatment has been effective, or whether a subject is experiencing a recurrence, or whether treatment resistance is emerging. In these embodiments, the methods include detecting the presence and/or level of MUC-1, HER2, EGFR, and EpCAM in samples obtained from a subject over time, e.g., in a first or baseline sample, and then in one or more subsequent samples. A decrease over time in the presence or levels of the biomarkers, e.g., a decrease in the quad biomarker value, indicates an improvement in the disease, e.g., that a treatment administered in the intervening time is effective to cause a decrease in cancerous cells or tumor burden. No change in the presence or levels of the biomarkers, e.g., no change in the quad biomarker value, indicates no change in disease, e.g., that any intervening treatment was not effective to cause a decrease in cancerous cells or tumor burden (though in particularly aggressive disease the treatment may have been effective to halt progression, which may be a treatment goal). A decrease over time in the presence or levels of the biomarkers, e.g., in the quad biomarker value, followed by a period of no change or an increase in the presence or levels of the biomarkers, e.g., in the quad biomarker value, indicates that any intervening treatment has lost effectiveness, and may indicate the presence of emerging resistance to the treatment.

An increase over time in the presence or levels of the biomarkers, e.g., an increase in the quad biomarker value, indicates that the disease is progressing, e.g., there has been an increase in cancerous cells or tumor burden. Such an increase may also be indicative of a poor prognosis, e.g., an increased likelihood of mortality.

Biomarkers—MUC-1, HER2, EGFR, and EpCAM

The methods described herein include the detection of four markers, i.e., MUC-1, HER2, EGFR, and EpCAM. The human sequences are set forth in Table A. Where a gene or protein has multiple isoforms, the use of reagents that bind to or detect the same isoform(s) as the antibodies listed in Table B, or that detect all or substantially all of the isoforms, is preferred.

TABLE A

| Gene Name | Nucleic Acid Sequence | Protein Sequence |
|---|---|---|
| MUC1 mucin 1, cell surface associated | Isoform 1 - NM_002456.5 | NP_002447.4 |
| | Isoform 2 - NM_001018016.2 | NP_001018016.1 |
| | Isoform 3 - NM_001018017.2 | NP_001018017.1 |
| | Isoform 5 - NM_001044390.2 | NP_001037855.1 |
| | Isoform 6 - NM_001044391.2 | NP_001037856.1 |
| | Isoform 7 - NM_001044392.2 | NP_001037857.1 |
| | Isoform 8 - NM_001044393.2 | NP_001037858.1 |
| | Isoform 9 - NM_001204285.1 | NP_001191214.1 |
| | Isoform 10 - NM_001204286.1 | NP_001191215.1 |
| | Isoform 11 - NM_001204287.1 | NP_001191216.1 |
| | Isoform 12 - NM_001204288.1 | NP_001191217.1 |
| | Isoform 13 - NM_001204289.1 | NP_001191218.1 |
| | Isoform 14 - NM_001204290.1 | NP_001191219.1 |
| | Isoform 15 - NM_001204291.1 | NP_001191220.1 |
| | Isoform 16 - NM_001204292.1 | NP_001191221.1 |
| | Isoform 17 - NM_001204293.1 | NP_001191222.1 |
| | Isoform 18 - NM_001204294.1 | NP_001191223.1 |
| | Isoform 19 - NM_001204295.1 | NP_001191224.1 |
| | Isoform 20 - NM_001204296.1 | NP_001191225.1 |
| | Isoform 21 - NM_001204297.1 | NP_001191226.1 |
| HER2 (ERBB2) verb- b2 erythroblastic leukemia viral oncogene homolog 2, neuro/lioblastoma derived oncogene homolog (avian) | Isoform a - NM_004448.2 | NP_004439.2 |
| | Isoform b - NM_001005862.1 | NP_001005862.1 |
| EGFR epidermal growth factor receptor | isoform a - NM_005228.3 | NP_005219.2 |
| | isoform b - NM_201282.1 | NP_958439.1 |
| | isoform c - NM_201283.1 | NP_958440.1 |
| | isoform d - NM_201284.1 | NP_958441.1 |
| EpCAM epithelial cell adhesion molecule | NM_002354.2 | NP_002345.2 |

In some embodiments, the methods include the use of antibodies or antigen fragments thereof, or oligonucleotides, that bind specifically (i.e., do not bind substantially to other molecules) to the biomarkers. The term "antibody" as used herein refers to an immunoglobulin molecule or an antigen-binding portion thereof. Examples of antigen-binding portions of immunoglobulin molecules include F(ab) and F(ab')$_2$ fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, *Antibodies: A Laboratory Manual* (1988); Goding, *Monoclonal Antibodies: Principles and Practice*, (N.Y. Academic Press 1983); Howard and Kaser, *Making and Using Antibodies: A Practical Handbook* (CRC Press; 1st edition, Dec. 13, 2006); Kontermann and Dübel, *Antibody Engineering Volume* 1 (Springer Protocols) (Springer; 2nd ed., May 21, 2010); Lo, *Antibody Engineering: Methods and Protocols (Methods in Molecular Biology)* (Humana Press; Nov. 10, 2010); and Dübel, *Handbook of Therapeutic Antibodies: Technologies, Emerging Developments and Approved Therapeutics*, (Wiley-VCH; 1 edition Sep. 7, 2010).

The antibody or oligonucleotide can be labeled, e.g., coupled to a detectable or imaging agent. Such agents are well known in the art and include paramagnetic agents, bioluminescent or fluorescent labels (e.g., GFP, FITC, rhodamine, or Texas Red), radioactive isotopes, and colorimetric/enzymatic agents (e.g., HRP, B-galactosidase). In a preferred embodiment, the antibody is coupled to a paramagnetic agent, e.g., a paramagnetic nanoparticle, e.g., monocrystalline iron oxide nanoparticle (MION), e.g., cross-linked iron oxide (CLIO) nanoparticles (CLIO has a MION core caged in cross-linked dextran); see, e.g., US 20110046004; Josephson et al., Bioconjug. Chem., 10(2): 186-91 (1999). Other paramagnetic agents include manganese-doped iron oxide nanoparticles (Mn-MNP) and elemental Fe core nanoparticles (cannonballs, CB), as well as micron-sized particles composed of many iron oxide cores embedded in a polymer matrix (see, e.g., Haun et al., Methods Mol Biol 726, 33-49 (2011), and references cited therein). The nanoparticles can be synthesized (e.g., as described in Josephson et al., (1999), supra, or Ly et al., Angew. Chem. Int. Ed. Engl. 46, 1222-1244 (2007)) or purchased commercially (e.g., from Miltenyi Biotec, Auburn, Calif.; Ocean NanoTech, Springdale, Ak.) and should have a polymer coating to render the core water soluble, prevent aggregation, and provide chemical functional groups for bioconjugation. The coating may comprise primary amine functional groups or by conjugated with proteins such as avidin or protein A. The antibodies can be coupled to the nanoparticles using, e.g., thiol chemistry or click chemistry, see, e.g., Haun et al., Methods Mol Biol 726, 33-49 (2011), Devaraj et al., Angew Chem Int Ed Engl 48, 7013-7016 (2009); Sun et al., IEEE J Solid-State Circuits 44, 1629 (2009); Sun et al., Mol. Imaging 5, 122-128 (2006); Haun et al., Nat. Nanotechnol. 5, 660-665 (2010); and Lee et al., Proc Natl Acad Sci USA 106, 12459-12464 (2009).

Other affinity agents, in addition to or as an alternative to antibodies, can also be used, e.g., peptides, small molecules, metal chelators, and natural biological binding partners, e.g., labeled EGF can be used to detect and quantitate EGFR.

Methods of Detection

The presence and/or level of a protein or transcript can be evaluated using methods known in the art, e.g., using quantitative immunoassay methods. In some embodiments, high throughput methods, e.g., protein or gene chips as are known in the art (see, e.g., Ch. 12, Genomics, in Griffiths et al., Eds. *Modern Genetic Analysis,* 1999, W. H. Freeman and Company; Ekins and Chu, Trends in Biotechnology, 1999, 17:217-218; MacBeath and Schreiber, Science 2000, 289 (5485):1760-1763; Simpson, *Proteins and Proteomics: A Laboratory Manual,* Cold Spring Harbor Laboratory Press; 2002; Hardiman, *Microarrays Methods and Applications: Nuts & Bolts,* DNA Press, 2003), can be used to detect the presence and/or level of MUC-1, HER2, EGFR, and EpCAM.

In some embodiments, the level of the protein or transcript is detected using an ultrasensitive and/or rapid assay. For example, the level of a protein can be detected using magnetic microparticle probes with antibodies that specifically bind the protein, see, e.g., Nam et al., Science 2003, 301:1884-1886.

A number of methods of detection that can be used in the present methods are set forth in FIGS. 10A-B.

In preferred embodiments, the methods include detecting levels of protein or transcript using diagnostic magnetic resonance (DMR), which uses magnetic nanoparticles (MNPs) as proximity sensors that modulate the transverse relaxation time of neighboring water molecules. This signal can be quantified using MR imagers or NMR relaxometers, including miniaturized NMR detector chips that are capable of performing highly sensitive measurements on microliter sample volumes and in a multiplexed format. In preferred embodiments, the methods include using a micro-NMR device as described herein and in Issadore et al., "Miniature magnetic resonance system for point-of-care diagnostics" Lab Chip, 2011, Advance Article DOI: 10.1039/ C1LC20177H (5 May 2011); U.S. Provisional Patent Application No. 61/466,135; and U.S. Provisional Patent Application entitled "Detection of Targets Using Magnetic Resonance", assigned Application No. 61/515,065, filed concurrently herewith and incorporated herein by reference in its entirety. Other preferred devices include the Benchtop NMR relaxometer (i.e., Minispec, Bruker Optics, Billerica, Mass.), and the miniaturized NMR (mNMR) detectors described in Lee et al., Nat Med 14, 869-874 (2008); Lee et al., Proc. Natl Acad. Sci. USA 106, 12459-12464 (2009); and Lee et al., Angew. Chem. Int. Ed. Engl. 48, 5657-5660 2009), as well as those described in WO 2009/045551; Haun et al., Methods Mol Biol 726, 33-49 (2011). Sun et al., IEEE ISSCC Digest Tech Papers 488-489 (2010); Sun et al., IEEE J Solid-State Circuits 44, 1629 (2009); and Liu et al., IEEE ISSCC Digest Tech Papers 140-141 (2008). All of the foregoing are incorporated herein by reference.

In some embodiments, microfluidic (e.g., "lab-on-a-chip") devices are used in the present methods. Such devices have been successfully used for microfluidic flow cytometry, continuous size-based separation, and chromatographic separation. In general, methods in which expression of the biomarkers is detected in circulating tumor cells (CTCs) can be used for the early detection of cancer, e.g., early detection of tumors of epithelial origin, e.g., pancreatic, lung, breast, prostate, renal, ovarian or colon cancer.

The devices can be used for separating CTCs from a mixture of cells, or preparing an enriched population of CTCs. In particular, such devices can be used for the isolation of CTCs from complex mixtures such as whole blood.

A variety of approaches can be used to separate CTCs from a heterogeneous sample. For example, a device can include an array of multiple posts arranged in a hexagonal packing pattern in a microfluidic channel upstream of a block barrier. The posts and the block barrier can be functionalized with different binding moieties. For example, the posts can be functionalized with anti-EPCAM antibody to capture circulating tumor cells (CTCs); see, e.g., Nagrath et al., Nature 450:1235-1239 (2007), optionally with downstream block barriers functionalized with to capture biomarker nucleic acids or proteins, or satellites. See, e.g., R. Weissleder et al., Nat. Med. 6, 351 (2000); R. Weissledera and M. J. Pittet, Nature 452, 580 (2008); H. Lee et al., Nat. Med. 14, 869 (2008) and the applications and references listed herein.

Processes for enriching specific particles from a sample are generally based on sequential processing steps, each of which reduces the number of undesired cells/particles in the mixture, but one processing step may suffice in some embodiments. Devices for carrying out various processing steps can be separate or integrated into one microfluidic system. The devices include devices for cell/particle binding, devices for cell lysis, devices for arraying cells, and devices for particle separation, e.g., based on size, shape, and/or deformability or other criteria. In certain embodiments, processing steps are used to reduce the number of cells prior to introducing them into the device or system. In some embodiments, the devices retain at least 75%, e.g., 80%, 90%, 95%, 98%, or 99% of the desired cells compared to the initial sample mixture, while enriching the population of desired cells by a factor of at least 100, e.g., by 1000, 10,000, 100,000, or even 1,000,000 relative to one or more non-desired cell types.

Some devices for the separation of particles rely on size-based separation with or without simultaneous cell binding. Some size-based separation devices include one or more arrays of obstacles that cause lateral displacement of CTCs and other components of fluids, thereby offering mechanisms of enriching or otherwise processing such components. The array(s) of obstacles for separating particles according to size typically define a network of gaps, wherein a fluid passing through a gap is divided unequally into subsequent gaps. Both sieve and array sized-based separation devices can incorporate selectively permeable obstacles as described above with respect to cell-binding devices.

Devices including an array of obstacles that form a network of gaps can include, for example, a staggered two-dimensional array of obstacles, e.g., such that each successive row is offset by less than half of the period of the previous row. The obstacles can also be arranged in different patterns. Examples of possible obstacle shapes and patterns are discussed in more detail in WO 2004/029221.

In some embodiments, the device can provide separation and/or enrichment of CTCs using array-based size separation methods, e.g., as described in U.S. Pat. Pub. No. 2007/0026413. In general, the devices include one or more arrays of selectively permeable obstacles that cause lateral displacement of large particles such as CTCs and other components suspended in fluid samples, thereby offering mechanisms of enriching or otherwise processing such components, while also offering the possibility of selectively binding other, smaller particles that can penetrate into the voids in the dense matrices of nanotubes that make up the obstacles. Devices that employ such selectively permeable obstacles for size, shape, or deformability based enrichment of particles, including filters, sieves, and enrichment or separation devices, are described in International Publication Nos. 2004/029221 and 2004/113877; Nagrath et al., Nature 2007, 450:1235-1239; Huang et al. Science 304:987-990 (2004), U.S. Publication No. 2004/0144651, U.S. Pat. Nos. 5,837,115 and 6,692,952, and U.S. Application Nos. 60/703,833, 60/704,067, and Ser. No. 11/227,904; devices useful for affinity capture, e.g., those described in International Publication No. 2004/029221 and U.S. application Ser. No. 11/071,679; devices useful for preferential lysis of cells in a sample, e.g., those described in International Publication No. 2004/029221, U.S. Pat. No. 5,641,628, and U.S. Application No. 60/668,415; devices useful for arraying cells, e.g., those described in International Publication No. 2004/029221, U.S. Pat. No. 6,692,952, and U.S. application Ser. Nos. 10/778,831 and 11/146,581; and devices useful for fluid delivery, e.g., those described in U.S. application Ser. Nos. 11/071,270 and 11/227,469. Two or more devices can be combined in series, e.g., as described in International Publication No. WO 2004/029221. All of the foregoing are incorporated by reference herein.

In some embodiments, a device can contain obstacles that include binding moieties, e.g., monoclonal anti-EpCAM, MUC1, EGFR, and/or HER2 antibodies or antigen-binding fragments thereof, that selectively bind to particular cell types, e.g., cells of epithelial origin, e.g., tumor cells. All of the obstacles of the device can include these binding moieties; alternatively, only a subset of the obstacles includes them. Devices can also include additional modules, e.g., a cell counting module or a detection module, which are in fluid communication with the microfluidic channel device. For example, the detection module can be configured to visualize an output sample of the device.

In one example, a detection module can be in fluid communication with a separation or enrichment device. The detection module can operate using any method of detection disclosed herein, or other methods known in the art. For example, the detection module includes a microscope, a cell counter, a magnet, a biocavity laser (see, e.g., Gourley et al., J. Phys. D: Appl. Phys., 36: R228-R239 (2003)), a mass spectrometer, a PCR device, an RT-PCR device, a microarray, or a hyperspectral imaging system (see, e.g., Vo-Dinh et al., IEEE Eng. Med. Biol. Mag., 23:40-49 (2004)). In some embodiments, a computer terminal can be connected to the detection module. For instance, the detection module can detect a label that selectively binds to cells, proteins, or nucleic acids of interest, e.g., EpCAM, MUC1, EGFR, and HER2 DNA, mRNA, or proteins.

In some embodiments, the microfluidic system includes (i) a device for separation or enrichment of CTCs; (ii) a device for lysis of the enriched CTCs; and (iii) a device for detection of EpCAM, MUC1, EGFR, and HER2 DNA, mRNA, or proteins.

Other microfluidic platforms have been described; see, e.g., Sun et al., Cancer Res 2010, 70:6128-6138.

Nanoassays can also be used, e.g., boron-doped silicon nanowires (SiNWs) can be used to create highly sensitive, real-time electrically based sensors for biological and chemical species, e.g., biotin-modified SiNWs can be used to detect streptavidin down to at least a picomolar concentration range, and antigen-functionalized SiNWs can be used to detect antibody binding and concentration, see, e.g., Cui et al., Science 2001, 293:1289-1292. Magnetic nanosensor technology can also be used; for example, magnetic nanosensors that are matrix insensitive yet still capable of rapid, multiplex protein detection with resolution down to attomolar concentrations are described in Gaster et al., Nature Medicine 1-7 2009, 15:1327-1332.

Methods of Treatment

In some embodiments, the methods described herein include the administration of a treatment for cancer to a subject who has been selected or identified as having cancer by a method described herein. Such treatments are known in the art and include surgical treatment (e.g., resection or debulking), chemotherapy, immunotherapy, radiotherapy, and others. See, e.g., Abraham et al., *The Bethesda Handbook of Clinical Oncology* (Lippincott Williams & Wilkins; Third edition, Sep. 4, 2009); Casciato and Territo, *Manual of Clinical Oncology* (Lippincott Manual Series) (Lippincott Williams & Wilkins; Sixth, North American Edition, Sep. 5, 2008); Haffty and Wilson, *Handbook of Radiation Oncology: Basic Principles and Clinical Protocols*, (Jones & Bartlett Publishers; 1st edition, Jul. 23, 2008); and Abeloff et al., *Abeloff's Clinical Oncology: Expert Consult* (Churchill Livingstone; 4 edition, May 21, 2008); Feig et al., *The M.D. Anderson Surgical Oncology Handbook* (Lippincott Williams & Wilkins; Fourth edition (Jun. 21, 2006).

Methods of Isolating Tumor Cells

The methods described herein can also be used to remove, enrich, or purify tumor cells from a sample. The sample is contacted with antibodies (or antigen binding fragments thereof) that bind to MUC1, EpCAM, HER2, and EGFR, where they bind to tumor cells. The antibodies are then used as "handles" to pull the cells out of the sample using known immunoaffinity separation methods. For example, if the antibodies are bound to MNPs, the sample can then be exposed to a magnetic field to separate the cells using methods known in the art. The cells could also be separated by exposing the sample to an agent that binds the antibodies, e.g., a protein A/G column or beads.

In some embodiments, using these methods, blood from a subject can be effectively "cleaned" of circulating tumor cells, and then returned to the subject, e.g., during hemodialysis.

Samples

In some embodiments of the present methods, the sample is or includes blood, or a portion or subfraction thereof, e.g., buffy coat comprising or suspected of comprising CTCs. In some embodiments, the sample comprises (or is suspected of comprising) CTCs. In some embodiments, the sample is or includes urine or a portion or subfraction thereof (e.g., a subfraction comprising or suspected of comprising CTCs). In some embodiments, the sample includes known or suspected tumor cells, e.g., is a biopsy sample, e.g., a fine needle aspirate (FNA), endoscopic biopsy, or core needle biopsy; in some embodiments the sample comprises cells from the pancreas, lung, breast, prostate, kidney, ovary or colon of the subject. In some embodiments, the sample comprises pleural fluid or paracentesis. In some embodiments, the sample comprises lung cells obtained from a sputum sample or from the lung of the subject by brushing, washing, bronchoscopic biopsy, transbronchial biopsy, or FNA, e.g., bronchoscopic, fluoroscopic, or CT-guided FNA (such methods can also be used to obtain samples from other tissues as well). In some embodiments, the sample is frozen, fixed and/or permeabilized; for example a tissue biopsy may be formalin-fixed paraffin-embedded (FFPE); a liquid sample may be fixed with various fixatives including formalin, formaldehyde, paraformaldehyde, glutaraldehyde, acetone or methanol.

EXAMPLES

The invention is further described in the following examples, which do not limit the scope of the invention described in the claims.

The following materials and methods were used in the Examples described herein:

Patient Population and Trial Design

Fifty subjects were enrolled from a consecutive series of patients who had been referred for clinical biopsy of an intra-abdominal lesion. The study was approved by the Massachusetts General Hospital (MGH) Institutional Review Board and informed consent was obtained from all participants. Computed tomography or ultrasound-guided FNA and core biopsies occurring within the MGH Abdominal Imaging and Intervention suites were conducted per routine. Subjects either had an established diagnosis of a solid epithelial cancer or an a priori suspicion of cancer, based on imaging results and the presence of tumor markers. One to two FNA passes were obtained and processed for µNMR analyses as described below. Two clinicians, who were blinded to the µNMR results, reviewed each subject's documented clinical, imaging, and pathology data. In rare instances where pathology was equivocal, data from repeat biopsies and/or follow-up radiographic imaging were used to reach a consensus on clinical outcome.

In a subset of patients with lesion diameters of at least 2 cm, additional FNA passes were performed to quantitate measurement reproducibility, to measure repeat regional and temporal heterogeneity or to compare µNMR measurements to FACS. To determine reproducibility, µNMR measurements were performed successively for each processed sample without further manipulation. Procedures for measuring repeat sampling heterogeneity involved performing repeated aspirations along the same coaxial needle pass (i.e. single lesion site) or by repositioning to a different region of the same lesion (i.e. multiple lesion sites). Temporal heterogeneity of samples was determined by obtaining and pooling multiple single lesion site FNAs, which were then aliquoted and preserved at 4° C. until processing at different timepoints.

To determine whether initial findings were generalizable, an independent test set containing an additional 20 subjects were enrolled. Samples from these patients were processed identically but only the four-marker panel (MUC-1+HER2+EGFR+EpCAM) was assayed.

Sample Processing.

Figure 9A:
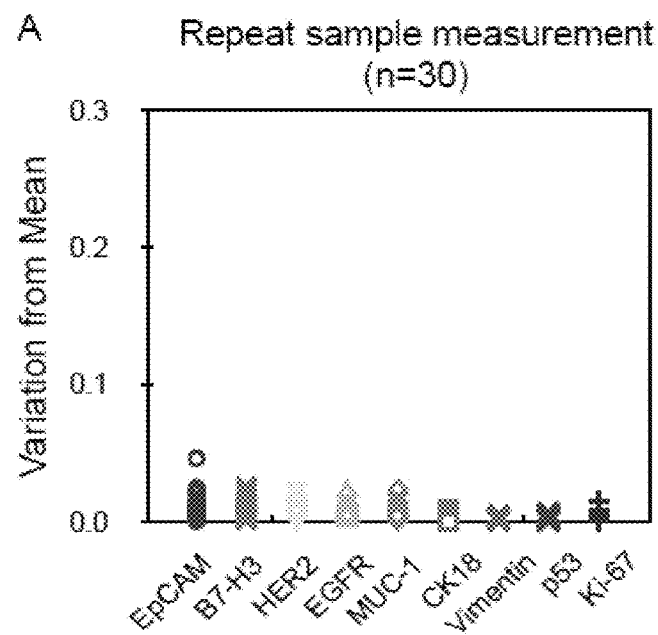
FIGS. 9A-C show the results of analysis of sample heterogeneity. (9A) Repeat measurement of the same samples (note the different scale compared to other graphs). (9B) Measurement of repeat FNA samples obtained via the same coaxial needle (see Table for variance component estimates for intra-subject variability). (9C) Measurement of repeat FNAs from different tumor sites.
Figure 9B:
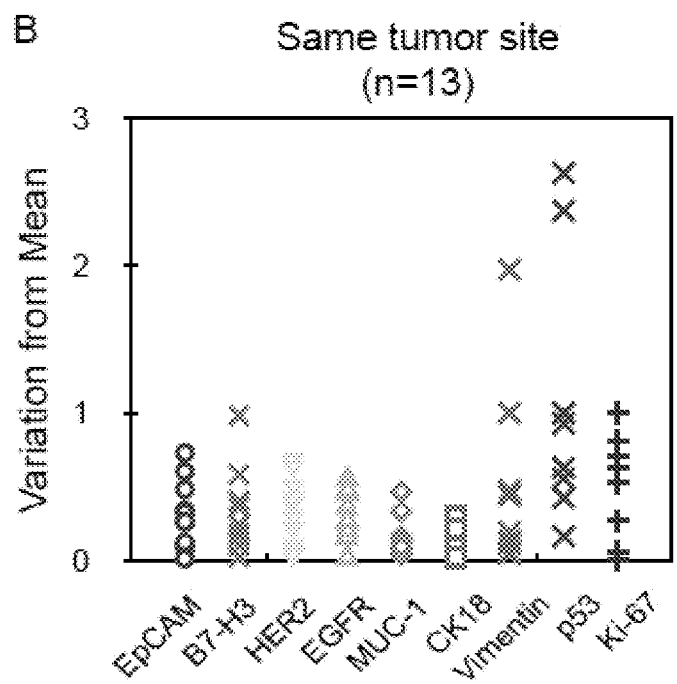
Figure 9C:
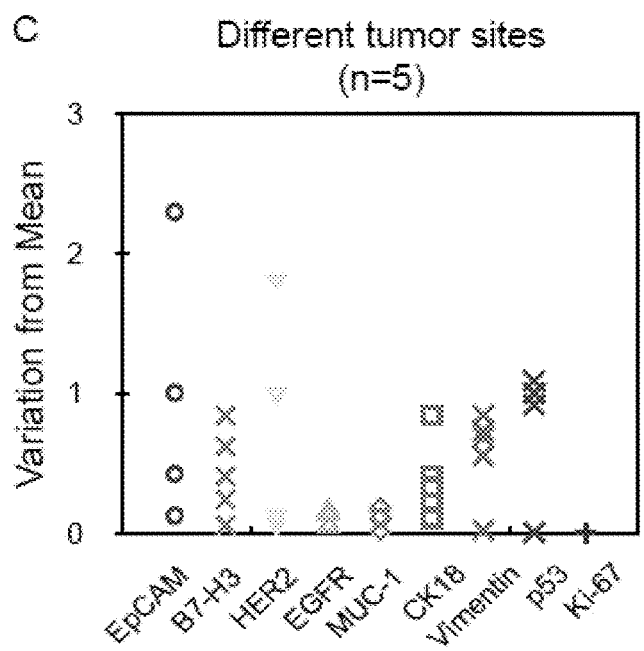
Figure 9D:
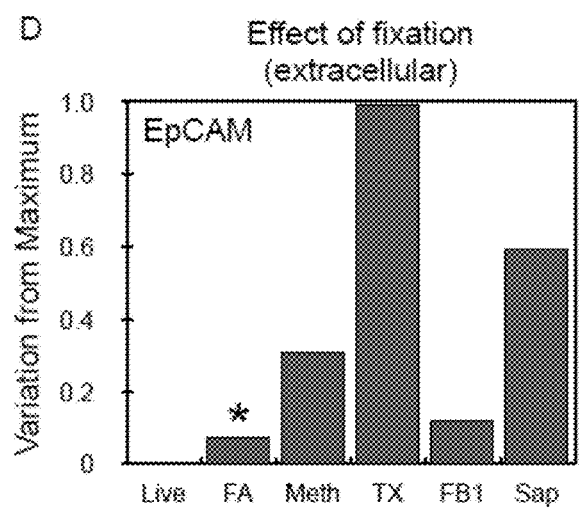
FIGS. 9D and 9E show the effect of prospective preservation treatments on extracellular and intracellular protein measurements. Live: live cells; FA: 2% formaldehyde; meth: 100% methanol; TX: triton X-100 0.05% in PBS, FB1: Fix buffer 1, BD Biosciences; Sap: saponin. *: optimized conditions chosen for subsequent experiments.
Figure 9E:
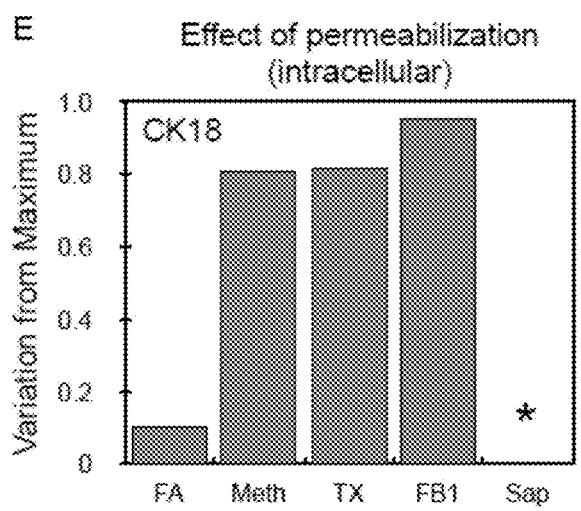

For each patient, FNA specimens were expelled into EDTA-coated Vacutainer tubes (BD Biosciences) using 2 mL saline for transport. Following centrifugation (400×g for 5 min) and resuspension, samples were divided into two separate groups for detection of extracellular or intracellular markers. We initially tested a variety of fixation and permeabilization protocols to optimize marker detection and to limit magnetic nanoparticle (MNP) background (FIGS. 9D and E). Based on results from these tests, the extracellular group was lightly fixed with 2% formaldehyde and the intracellular group was fixed with Fix Buffer 1 (FB1, BD Biosciences) and semi-permeabilized with saponin (Perm/Wash buffer, BD Biosciences) as per the manufacturer instructions.

Preparation of Trans-Cyclocten (TCO)-Modified Antibodies.

Monoclonal antibodies against proteins of interest (see Table B) were reacted with (E)-cyclooct-4-enyl 2,5-dioxopyrrolidin-1-yl carbonate (TCO-NHS), which was synthesized as previously reported (53). The reaction was performed using 0.25 to 0.5 mg of antibody and 1000 equivalents of TCO-NHS in 10% dimethylformamide (DMF) for 3 hours at room temperature. Unreacted TCO-NHS was then removed using 2 mL Zeba desalting columns (Thermo Fisher), and antibody concentration was determined by absorbance measurement. TCO valencies were determined based on changes in molecular weight using MALDI-TOF (matrix-assisted laser desorption/ionization-time-of-flight) mass spectrometry (24). Briefly, the antibody was diluted to 150 µg/mL using water and combined at a ratio of 2:1 with sinapinic acid (1 mg dissolved in 0.1 mL 70/30 acetonitrile/water with 0.1% trifluoroacetic acid; Thermo Fisher). 1 µL was then dried onto a sample plate. Data was collected using a Voyager-DE BioSpectrometry Workstation MALDI-TOF mass spectrometer (Applied Biosystems) and analyzed using a custom MATLAB (MathWorks) program. The number of TCO modifications per antibody was then calculated based on the difference in molecular weight compared to the unmodified antibody, and by assuming that a 152.2 dalton net mass was added per TCO (Table B) (24). Variations in TCO loading were likely the result of differences in the availability of amine sites between different species and IgG subclasses.

TABLE B

Complete list of antibodies and associated characteristics relevant to the study

| Marker | Clone | Species | Isotype | MW | MW (TCO) | TCO Valency | Company |
| --- | --- | --- | --- | --- | --- | --- | --- |
| Control | MOPC-21 | Mouse | $IgG_1$ | 151,700 ± 200 | 153,100 ± 100 | 9.1 | BioLegend |
| CD45 | H130 | Mouse | $IgG_1$ | 149,200 ± 100 | 150,600 ± 100 | 8.9 | BioLegend |
| EpCAM | 158206 | Mouse | $IgG_{2b}$ | 150,600 ± 300 | 152,100 ± 200 | 9.7 | R&D Systems |
| B7-H3 | 185504 | Mouse | $IgG_1$ | 152,400 ± 100 | 153,600 ± 100 | 7.4 | R&D Systems |
| HER2 | Trastuzumab | Human | $IgG_1$ | 148,700 ± 300 | 152,300 ± 400 | 23.2 | Genentech |
| EGFR | Cetuximab | Human/Mouse | NA | 152,400 ± 300 | 153,800 ± 200 | 9.2 | Imclone Systems |
| MUC-1 | M01102909 | Mouse | $IgG_1$ | 151,900 ± 200 | 152,600 ± 200 | 4.8 | Fitzgerald Industries |
| CK18 | DA-7 | Mouse | $IgG_1$ | 150,000 ± 100 | 150,800 ± 100 | 4.8 | EXBIO |
| Vimentin | V9 | Mouse | $IgG_1$ | 149,500 ± 200 | 153,800 ± 100 | 28.4 | Lab Vision |
| p53 | 1C12 | Mouse | $IgG_1$ | 152,300 ± 200 | 153,700 ± 200 | 9.1 | Cell Signaling |
| Ki-67 | B56 | Mouse | $IgG_1$ | 148,100 ± 100 | 151,800 ± 200 | 24.4 | BD Biosciences |

Preparation of Tetrazine (Tz) Modified Magnetic Nanoparticles (MNPs).

Cross-linked iron oxide (CLIO) nanoparticles were prepared as described previously (J. M. Perez et al., Nat. Biotechnol. 20, 816 (2002)). Briefly, 3 nm monocrystalline cores composed of $(Fe_2O_3)_n(Fe_3O_4)m$ were synthesized within a matrix of 10 kDa dextran. These were cross-linked with epichlorohydrin and reacted with ammonia to produce MNPs with primary amine groups ($NH_2$-MNPs). The number of amines per MNP was approximately 89, as determined by reaction with N-succinimidyl 3-(2-pyridyldithio) propionate (SPDP; Thermo Fisher) and dithiothreitol. The hydrodynamic diameter was 28.8 nm, as measured by dynamic light scattering (Zetasizer 1000HS; Malvern Instruments). At 40° C. and 0.47 T (Minispec MQ20; Bruker), the $R_1$ and $R_2$ relaxivities were 25.2 $mM^{-1}$ $s^{-1}$ and 64.5 $mM^{-1}$ $s^{-1}$, respectively. Tz-MNPs were created by reacting $NH_2$-MNPs with 500 equivalents of 2,5-dioxopyrrolidin-1-yl 5-(4-(1,2,4,5-tetrazin-3-yl)benzylamino)-5-oxopentanoate (Tz-NHS), synthesized as previously reported (24). This reaction proceeded in PBS containing 5% DMF for 3 hours at room temperature. Excess Tz-NHS was removed by gel filtration using Sephadex G-50 (GE Healthcare). Tz-MNP concentration was determined by absorbance measurement at 410 nm using a known standard for calibration. MNP molar concentration was then determined based on an estimated molecular weight of 447,000 dalton (8000 Fe atoms per core crystal, 55.85 dalton per Fe atom (F. Reynolds, Anal. Chem. 77, 814 (2005))). Tz-MNPs were stable at pH 6.5 for several months as determined by analytical methods.

MNP Targeting and Detection by Nuclear Magnetic Resonance.

Each specimen was divided into aliquots in microcentrifuge tubes and incubated with TCO-modified monoclonal antibodies (10 μg/mL) in 0.15 ml of the appropriate buffer (extracellular samples: PBS containing 1% BSA, or PBS+; intracellular samples: saponin-based Perm/Wash from BD Biosciences containing 1% BSA, or PW+) for 10 minutes at room temperature. Samples were then pelleted by centrifugation, aspirated, and resuspended directly with Tz-MNP (100 nM). After incubating for 30 minutes at room temperature on a rotator, samples were washed twice by centrifugation with PBS+ or PW+, washed once with PBS, and then resuspended in 20 μL PBS.

Cell Lines Used for Marker Calibration

Calibration curves were created using the human cancer cell lines SK-BR-3, PANC-1, SK-OV-3, HT-29, A549, A431, and NCI-H1650 that were obtained from ATCC. Cell lines were maintained in Dulbecco's modified Eagle's medium (DMEM) supplemented with 10% fetal bovine serum (FBS) and 5% penicillin/streptomycin. Human adult dermal fibroblasts (HDF) were maintained in Medium 106 with Low Serum Growth Supplement (all from Invitrogen). Before treatment, tumor and HDF cells were grown to ~90% confluency, released using 0.05% Tryspin/0.53 mM ethylenediaminetetraacetic acid (EDTA), and washed twice by centrifugation with phosphate buffered saline containing 1% bovine serum albumin (PBS+). Human leukocytes were obtained from fresh peripheral blood drawn from three healthy volunteers via venipuncture and stored in EDTA-coated VacuTainer collection tubes (BD Biosciences). Red blood cells were lysed using PharmLyse (BD Biosciences) and the remaining leukocytes were washed twice by centrifugation with PBS+.

Cell Treatments and NMR Measurements

Before treatment, suspended cells were fixed with formaldehyde (for extracellular markers) or semi-permeabilized with saponin (for intracellular markers), labeled with magnetic nanoparticles (MNPs), and detected using the μMR, as described herein. Each cell type was tested for background MNP binding using a control antibody, and assayed at three different cell concentrations (2500, 1000, and 500 tumors cells and fibroblasts; 10000, 2500, and 1000 leukocytes). This provided correlation factors for converting the control NMR signals into actual cell numbers (see calculations below and FIG. 2A). The tumor markers EpCAM (epithelial cell adhesion molecule), B7-H3 (B7 homolog 3), HER2 (human epidermal growth factor receptor 2), EGFR (epidermal growth factor receptor), MUC-1 (Mucin-1), CK18 (cytokeratin 18), vimentin, p53, and Ki-67 were measured in three cell lines displaying relatively high, medium, and low expression levels. The cell line with the highest expression level was measured at the same cell concentrations indicated above for the background binding measurement (2500, 1000, and 500 cells). The cell line with medium expression level was measured at two cell concentrations (2500 and 1000 cells) and the low level at only one concentration (2500 cells). This provided additional data for fitting expression level per cell, and ensured that there was no bias in the calibrations towards cell concentration. Fibroblasts were assessed for all markers at the high concentration to determine whether there was overlap in expression. Leukocytes were assessed for CD45 at the same concentrations used for controls, but only at the high concentration for each tumor marker.

Confirmation of Biomarker Expression Levels by Flow Cytometry

Molecular expression levels for EpCAM, B7-H3, HER2, EGFR, MUC-1, CK18, vimentin, p53, and Ki-67 were measured by flow cytometry using fluorescent antibodies for each cell type analyzed by magnetic resonance. Fixed or permeabilized cells (106/sample) were incubated with 1 µg/mL primary antibody in 0.15 ml PBS+ or PW+ for 15 minutes at room temperature. The primary antibodies employed were the same as those used for targeting nanoparticles in their unmodified form (see Table B). Samples were then washed with ice-cold PBS+ or PW+ and incubated with the appropriate monoclonal, fluorescein-conjugated secondary antibody (anti-mouse IgG1, BD Biosciences; antimouse IgG2a/b, BD Biosciences; anti-rabbit IgG, Sigma Aldrich) at 1 µg/mL for 30 minutes on ice. Following two washes with ice-cold PBS+ or PW+, fluorescein fluorescence intensity was measured using an LSRII flow cytometer. Fluorescence intensities were converted to the number of markers per cell using Quantum Simply Cellular anti-mouse antibody beads (Bangs Labs), which were similarly incubated with each primary and secondary antibody pair. Since anti-rabbit calibration beads were not available, the fluorescence correlation factor for the anti-rabbit secondary antibody was estimated based on the number of fluorescein molecules per antibody, as measured by absorbance at 488 nm, relative to the anti-mouse secondary antibodies.

The µNMR Device and its Operation

In this study, a new µNMR system (DMR-3) specifically intended for clinical applications was used. The µNMR system conceptually consists of solenoidal microcoils, a portable magnet, and custom-built NMR hardware (see Issadore et al., "Miniature magnetic resonance system for point-of-care diagnostics" Lab Chip, 2011, Advance Article DOI: 10.1039/C1LC20177H (5 May 2011). To maximize the sample filling factor (≈1) and hence the NMR signal level, the solenoidal coils were embedded in polydimethylsiloxane (PDMS) along with the fluidic channels. Samples were either directly injected to the fluidic channels, or were contained in thin-walled (thickness: 25 µm) tubes which were then inserted into the coil bores. The coils were mounted on a printed circuit board containing impedance matching networks and multiplexers. A polarizing magnetic field (0.5 T) was generated by a portable, permanent magnet (PM1055-050N, Metrolab). The NMR hardware houses a digital signal processor (DSP) unit (C2000 series, Texas Instruments), a radio frequency (RF) generator (AD9954, Analog Devices) and an analog-to-digital converter (AD7690, Analog Devices). The DSP unit controls the entire operation of the system, and communicates with an external smartphone for user-inputs. For robust NMR measurements, the DPS unit was programmed to maintain a constant offset between two frequencies: the NMR frequency (determined by the external magnetic field) and the RF carrier (for excitation). The transverse relaxation rate ($R_2$) was measured within the 1 µl sample volume of the microcoil using Carr-Purcell-Meiboom-Gill pulse sequences with the following parameters: echo time (TE): 4 ms; repetition time (TR): 6 s; the number of 180° pulses per scan: 500; the number of scans: 8. $R_2$ values were subtracted from the $R_2$ value for PBS alone to obtain $\Delta R_2$. Marker levels were calculated as follows.

Determination of Tumor Cell Concentration and Marker Expression Level

Since nonspecific association of MNPs with tumor cells has been shown to be consistent across different tumor cell lines (Lee et al., Proc. Natl. Acad. Sci. U.S.A. 106, 12459 (2009)), the total cell count per sample was estimated based on the control $\Delta R_2$ value)($\Delta R_2^\theta$) that had been determined for subset of samples that was assayed for extracellular markers (i.e. fixed with formaldehyde). Absolute cell numbers were then determined using calibration curves of $\Delta R2$ versus cell concentration. However, correction was required to account for the variable presence of leukocytes residing in the tumor or introduced into the sample along with blood during procurement. This problem was approached by separating $\Delta R2^\theta$ into leukocyte ($\Delta R_{2L}^\theta$) and non-leukocyte ($\Delta R_{2N}^\theta$) components $$\Delta R_{2\theta} = \Delta R_{2L}^\theta + \Delta R_{2N}^\theta. \quad (1)$$

Figure 2A:
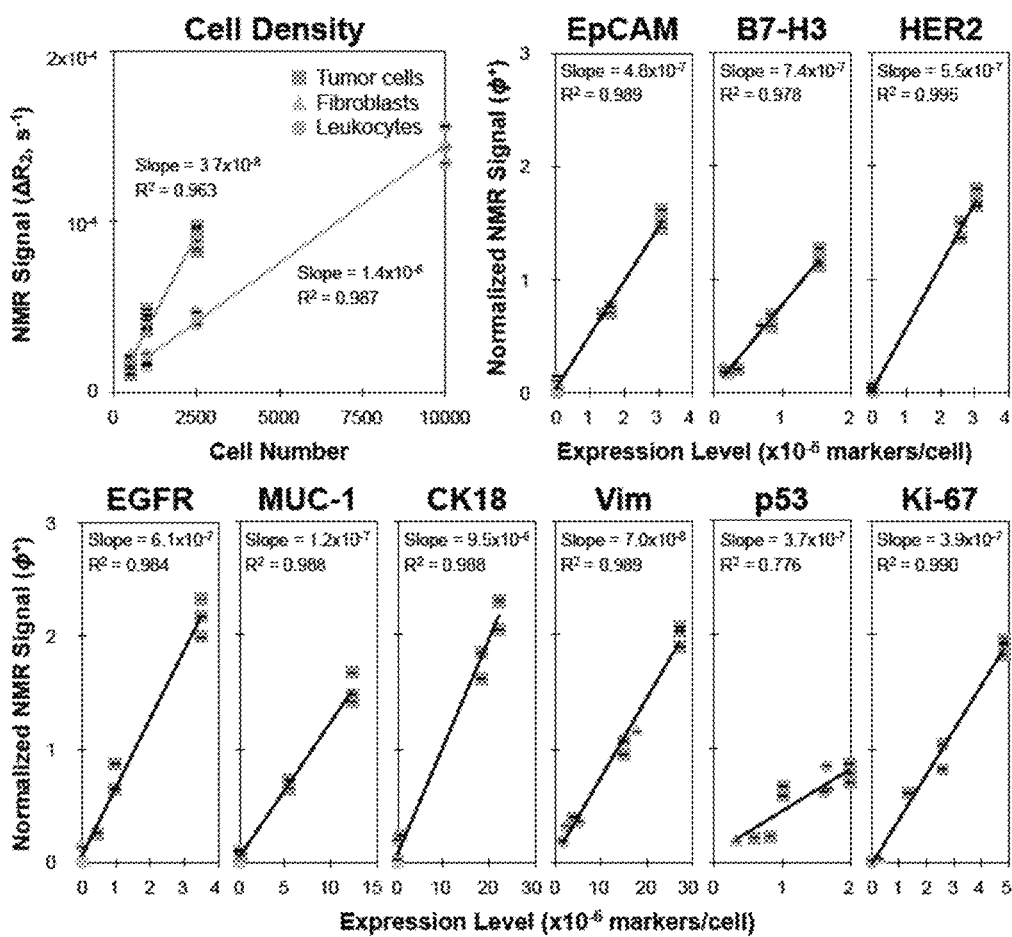
FIG. 2A is a set of calibration curves correlating μNMR signals with molecular expression levels for cell lines.

It is important to note that $\Delta R_{2N}^\theta$ includes not only tumor cells but also normal epithelial, stromal, or resident inflammatory cells. Eq. (1) could be further expanded to include these other cell types if appropriate unique recognition markers were incorporated. When a sample contains nL leukocytes and nN non-leukocytes, Eq. (1) can be rewritten as $$\Delta R_2^\theta = r_{2L}^\theta \cdot n_L + r_{2N}^\theta \cdot n_N, \quad (2)$$

where $r_{2L}^\theta$ and $r_{2N}^\theta$ are the cellular relaxivities for leukocytes and non-leukocytes, respectively, from non-specific binding. These values were predetermined from the calibration curves generated using a single-cell population (FIG. 2A). Note that $r_{2N}^\theta$ values were similar for numerous tumor cell lines as well as for human dermal fibroblasts.

For each FNA sample, aliquots were separately probed for various cancer markers (+) as well as for the leukocyte content (CD45) and total cell density (θ). These resulted in three observables:

$$\Delta R_2^+ = r_{2L}^+ \cdot n_L + r_{2N}^+ \cdot n_N \quad (3)$$
$$\simeq r_{2L}^\theta \cdot n_L + r_{2N}^+ \cdot n_N$$

$$\Delta R_2^{CD45} = r_{2L}^{CD45} \cdot n_L + r_{2N}^{CD45} \cdot n_N \quad (4)$$
$$\simeq r_{2L}^{CD45} \cdot n_L + r_{2N}^\theta \cdot n_N$$

$$\Delta R_2^\theta = r_{2L}^\theta \cdot n_L + r_{2N}^\theta \cdot n_N \quad (5)$$

Since CD45 is a unique and ubiquitous marker for leukocytes, fresh peripheral blood leukocytes obtained from healthy volunteers were used to obtain $r_{2L}^{CD45}$. Thus, from Eqs. (4) and (5), $n_L$ and $n_N$ (the cell numbers for leukocytes and nonleukocytes) could be estimated:

$$\begin{pmatrix} n_L \\ n_N \end{pmatrix} = \begin{pmatrix} r_{2L}^{CD45} & r_{2N}^\theta \\ r_{2L}^\theta & r_{2N}^\theta \end{pmatrix}^{-1} \begin{pmatrix} \Delta R_2^{CD45} \\ \Delta R_2^\theta \end{pmatrix}. \quad (6)$$

By inserting the numbers derived from Eq. (6) into Eq. (3), the cellular relaxivity of the cancer marker (+) for non-leukocyte cells could then be obtained:

$$r_{2N}^+ = \frac{\Delta R_2^+ - r_{2L}^\theta \cdot n_L}{n_N}. \quad (7)$$

The expression level of a marker (+) is defined as $$\phi_N^+ = \frac{r_{2N}^+}{r_{2N}^\theta} - 1 = \frac{\Delta R_2^+ - r_{2L}^\theta \cdot n_L}{r_{2L}^\theta \cdot n_N} - 1, \quad (8)$$

in which Eqs. (6) and (7) are used to obtain values, including predetermined values for $r_{2L}^\theta$, $r_{2N}^\theta$, and $r_{2L}^{CD45}$.

Values for φN⁺ were converted to molecular expression level per cell using calibration curves constructed from multiple cell lines with varying expression (FIG. 2A). Since only one species is present in these model systems, Eq. (8) can be represented as $$\phi_{ref}^+ = \frac{r_{2N}^+}{r_{2N}^\theta} - 1, \quad (9)$$

To generate correlation factors, the values for $\phi_{ref}^+$ were plotted against the corresponding expression level for each cell type as measured by flow cytometry (FIG. 2A).

Statistics

The Spearman correlation coefficient was used to assess the correlations between different variables, and the non-parametric Mann-Whitney test was used to determine the magnitudes of between-group differences. Random effects models were used to separate within-subject variability (reproducibility of the NMR measurements) from between-subject variability. Receiver operating characteristic (ROC) curves were constructed for individual markers and selected marker combinations by plotting sensitivity versus 1-specificity and calculated the areas under the ROC curves (Az). An Az=0.5 was used to indicate that the test shows no difference between the two groups while an Az=1.0 was used to indicate that the test gives a perfect separation between the groups. When assessing discrimination accuracy of marker combinations, logistic regression was first used to estimate a risk score function and then constructed the ROC curves based on this risk score function. The optimal cutoff value for identifying malignant status was defined as the point on the ROC curve with the minimal distance between the 0% false-negative and the 100% true-positive rate. Sensitivity, specificity, and accuracy were calculated using standard formulas. A "leave-one-out" cross-validation method was also employed to calculate prediction accuracy for a future patient. Specifically, one sample was omitted before selecting the optimal cutoff point using the remaining samples. This was repeated until every sample had been left out once and then the prediction accuracy was calculated based on the accuracy rates for the left-out samples. The bootstrap method was used to estimate the standard errors for the prediction accuracy rates estimated from the "leave-one-out" cross-validation. All tests were two-sided and a P-value less than 0.05 was considered statistically significant. All µNMR and MALDI-TOF measurements were performed in triplicate and the data are presented as the mean±standard error.

Example 1. Quantitation of Cellular Samples

A total of 50 patients, presenting with suspected abdominal malignancies and referred for routine biopsy, were initially enrolled in the study. Of these, 44 patients' lesions were ultimately malignant and 6 patients' lesions were benign, as determined by repeat core biopsies, serial follow-ups, imaging (including PET-CT), and/or from clinical information (Table 1).

TABLE 1

Clinical information for 70 patients with suspected abdominal malignancies

| Characteristic | Original diagnostic set | | Independent test set | |
|---|---|---|---|---|
| | Number | % | Number | % |
| Number of patients | 50 | | 20 | |
| Age | | | | |
| Median | 64 | | 63 | |
| Range | 29-86 | | 24-90 | |
| Gender | | | | |
| Male | 24 | 48% | 7 | 35% |
| Female | 26 | 52% | 13 | 65% |
| Lesion type | | | | |
| Malignant | 44 | 88% | 14 | 70% |
| Benign | 6 | 12% | 6 | 30% |
| Tumor Subtypes | | | | |
| Breast | 2 | 4.5% | 2 | 14% |
| Gastrointestinal | 13 | 30% | 4 | 28% |
| Genitourinary | 3 | 6.5% | 1 | 7% |
| Gynecologic | 4 | 9% | 3 | 22% |
| Lung | 8 | 18% | 1 | 7% |
| Pancreatic | 7 | 16% | 3 | 22% |
| Undifferentiated | 7 | 16% | 0 | 0% |
| History | | | | |
| Prior history of cancer | 30 | 60% | 4 | 20% |
| No prior therapies | 20 | 42% | 7 | 35% |
| Active treatment | 11 | 22% | 9 | 45% |
| Biopsy Site† | | | | |
| Visceral | 36 | 72% | 9 | 45% |
| Non-visceral | 14 | 28% | 11 | 55% |
| Lesion Size (axial dia.) | | | | |
| <1 cm | 3 | 6% | 10 | 50% |
| 1-3 cm | 25 | 50% | 6 | 30% |
| >3 cm | 22 | 44% | 4 | 20% |
| Biopsy Modality | | | | |
| Ultrasound | 14 | 28% | 16 | 80% |
| CT | 36 | 72% | 4 | 20% |

Figure 2B:
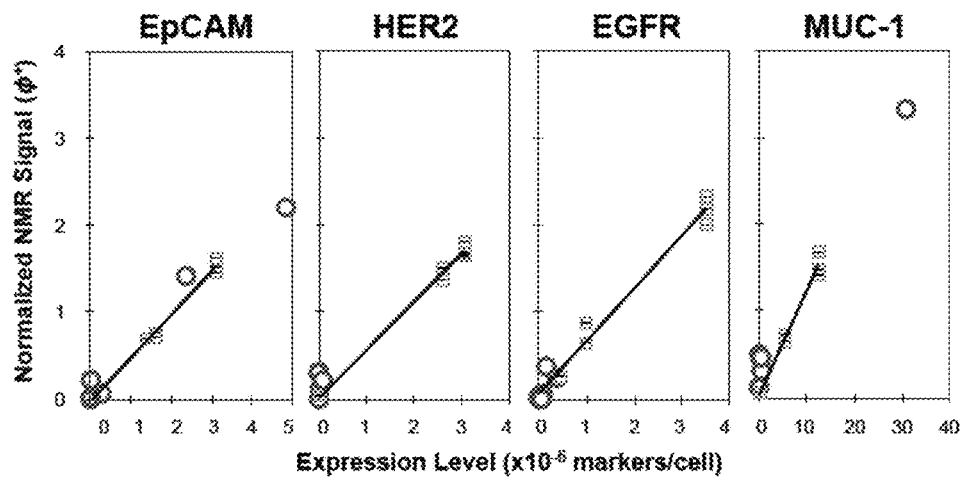
FIG. 2B is a set of correlative μNMR and FACS measurements for 5 clinical patient samples.

For each patient, a 1-2 pass FNA sample was obtained using a 22 G needle. This was followed by a series of routine core biopsies (17 G) for conventional standard-of-care analysis. In selected patients, additional FNA samples were obtained to further quantify sample heterogeneity and to validate these measurements against accepted gold standards (see below). Each FNA sample was washed with 1-2 mL of buffered saline and processed for µNMR for subsequent measurement of 11 variables: 9 cancer related markers (EpCAM, MUC-1, HER2, EGFR, B7-H3, CK18, Ki-67, p53, and Vimentin), a CD45 count, and the total cell density. A priori selection of these protein markers were based on current practice (e.g. EpCAM and CK18) (S. Nagrath et al., Nature 450, 1235 (2007); L. V. Sequist et al., J. Thorac. Oncol. 4, 281 (2009)) or on reports of clinically relevant over-expression (S. B. Ho et al., Cancer Res. 53, 641 (1993); C. L. Vogel et al., J. Clin. Oncol. 20, 719 (2002); T. J. Roth et al., Cancer Res. 67, 7893 (2007)). To maximize detection sensitivity, a highly efficient bioorthogonal approach was adapted for sensing that uses trans-cyclooctene (TCO)/tetrazine (Tz) chemistry (J. B. Haun et al., Nat. Nanotechnol. 5, 660 (2010)). Curves calibrating µNMR signals with cellular expression levels for each of the markers were obtained prior to the study (see FIG. 2A). The µNMR-derived measurements of markers in clinical samples correlated well against accepted gold standards (FIGS. 1 and 2A-B). For example, the correlation coefficient between µNMR and ELISA measurements for EGFR, a clinically important marker, was 0.99 (FIG. 1).

Figure 3:
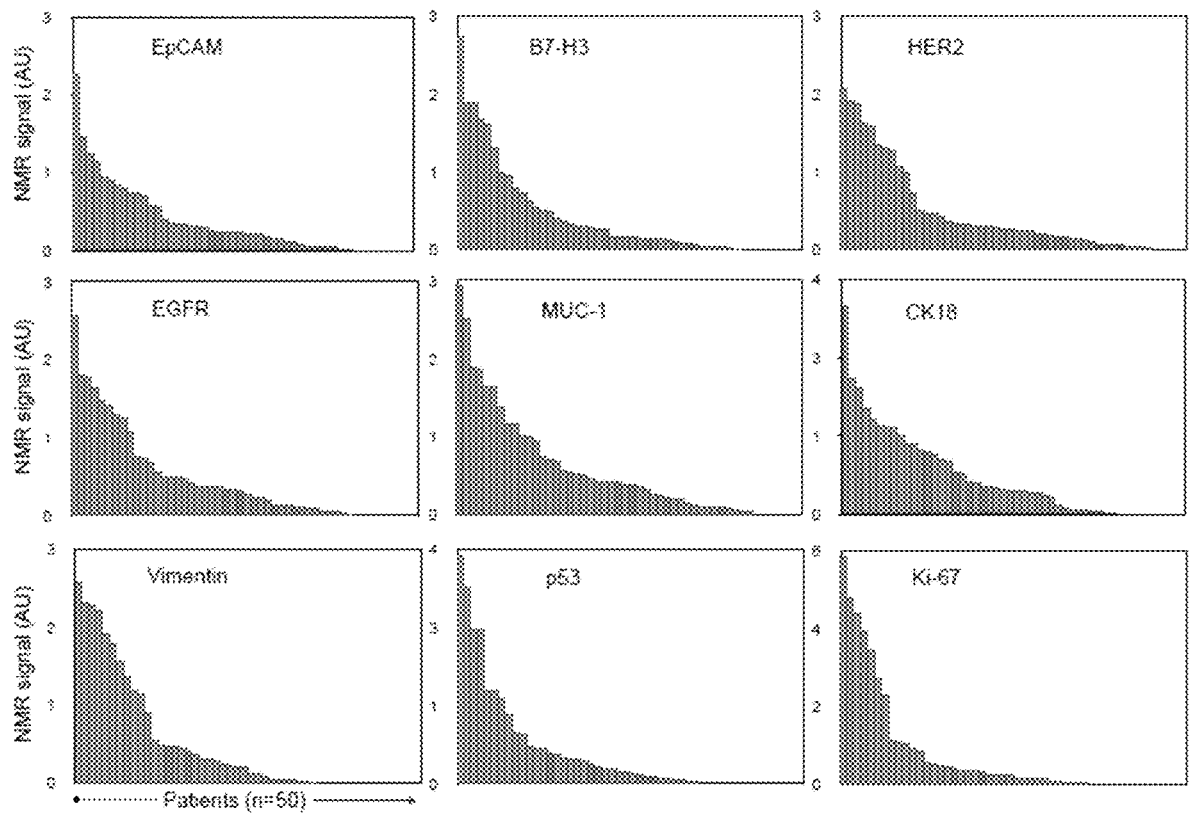
FIG. 3 is a set of 9 graphs illustrating biomarker expression level distribution. Waterfall plots showing the expression levels of each of the different biomarkers sorted from high (left) to low (right). Each column represents a different patient sample (lighter grey=malignant; darker grey=benign).

All FNA samples yielded sufficient cell numbers for subsequent µNMR analysis. On average, 3,866±456 cells were obtained per patient. Of these, approximately one-third were CD45-positive leukocytes (1,354±207 cells). The remaining cells were non-leukocytic, primarily tumor cells (as determined by extensive FACS analysis in optimization studies), and these were aliquoted into samples containing an average of ~200 cells for each of the 9 biomarker measurements. To determine the global expression levels of each marker, waterfall plots were created to determine overall distribution (FIG. 3). As expected, there was a spectrum of marker expression with approximately one-third of samples each showing high, intermediate, and low or absent protein levels, respectively. Benign samples typically fell into the latter two categories.

Figure 4:
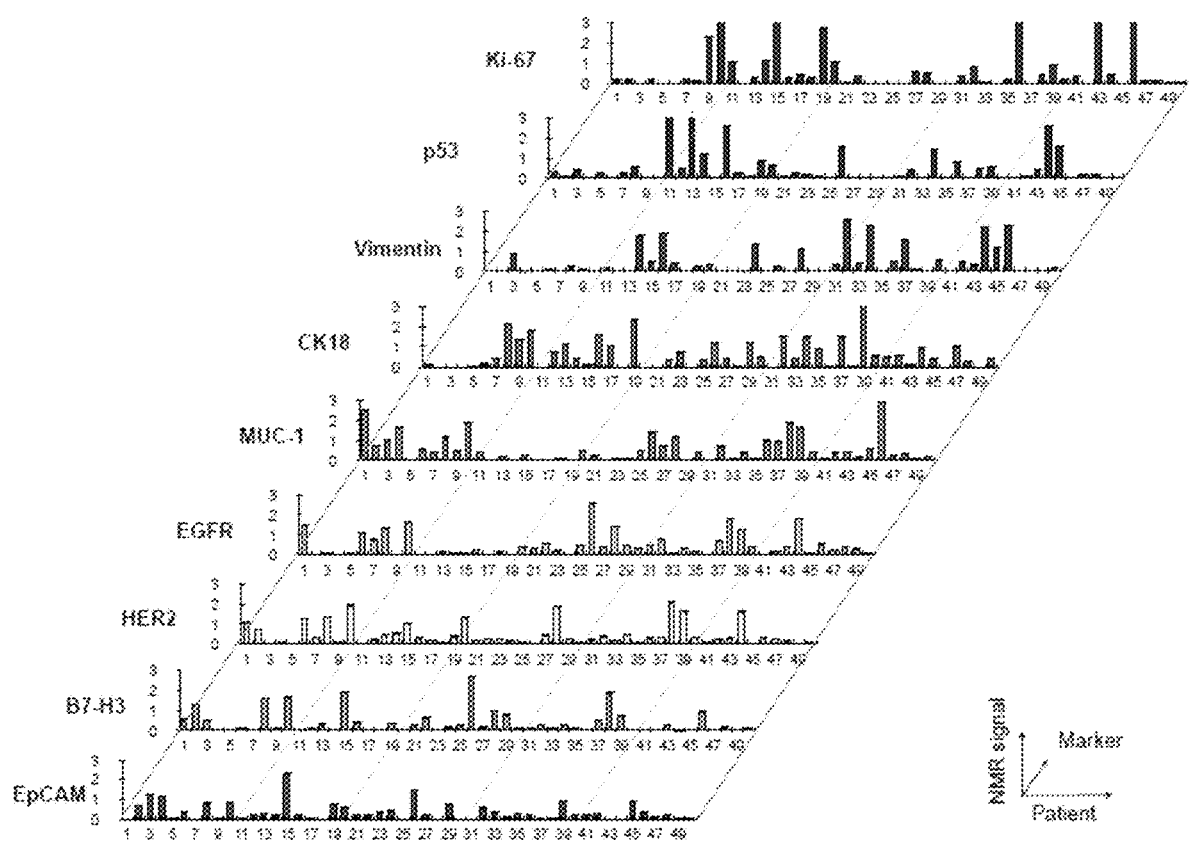
FIG. 4 is a set of graphs showing expression levels of different biomarkers arranged by patient number. Patients 5, 12, 17, 18, 21, 42 had benign lesions.
Figure 5:
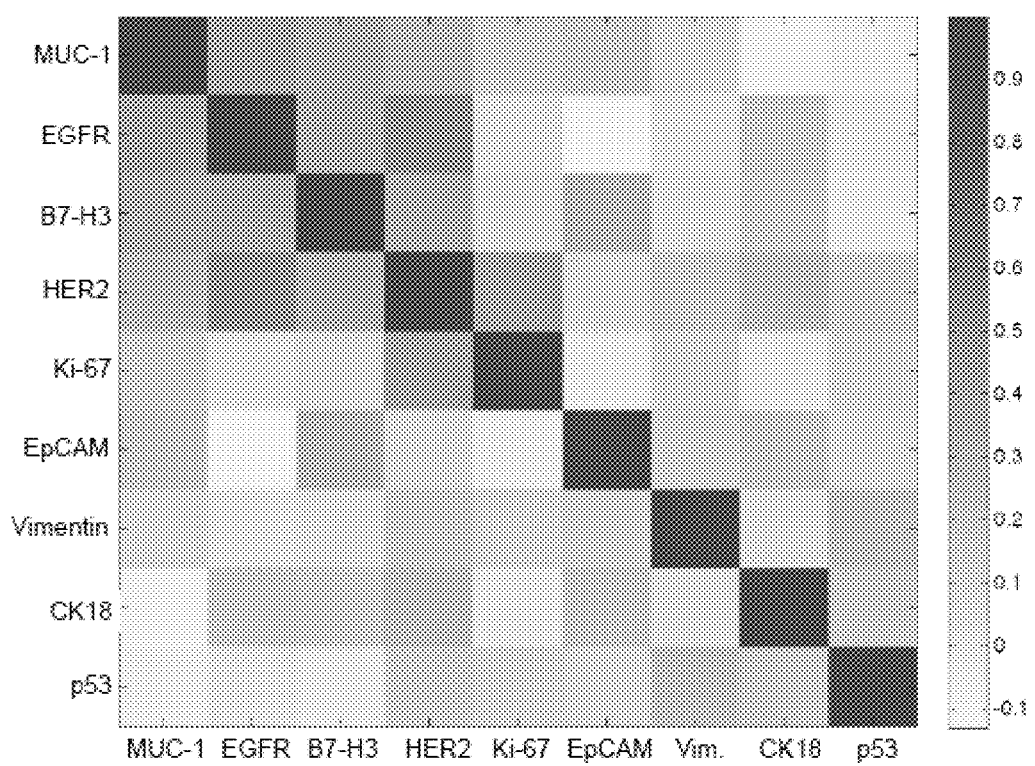
FIG. 5 is a graphical representation of the Spearman correlation coefficients (0: no correlation, 1: perfect correlation) between markers.
Figure 6:
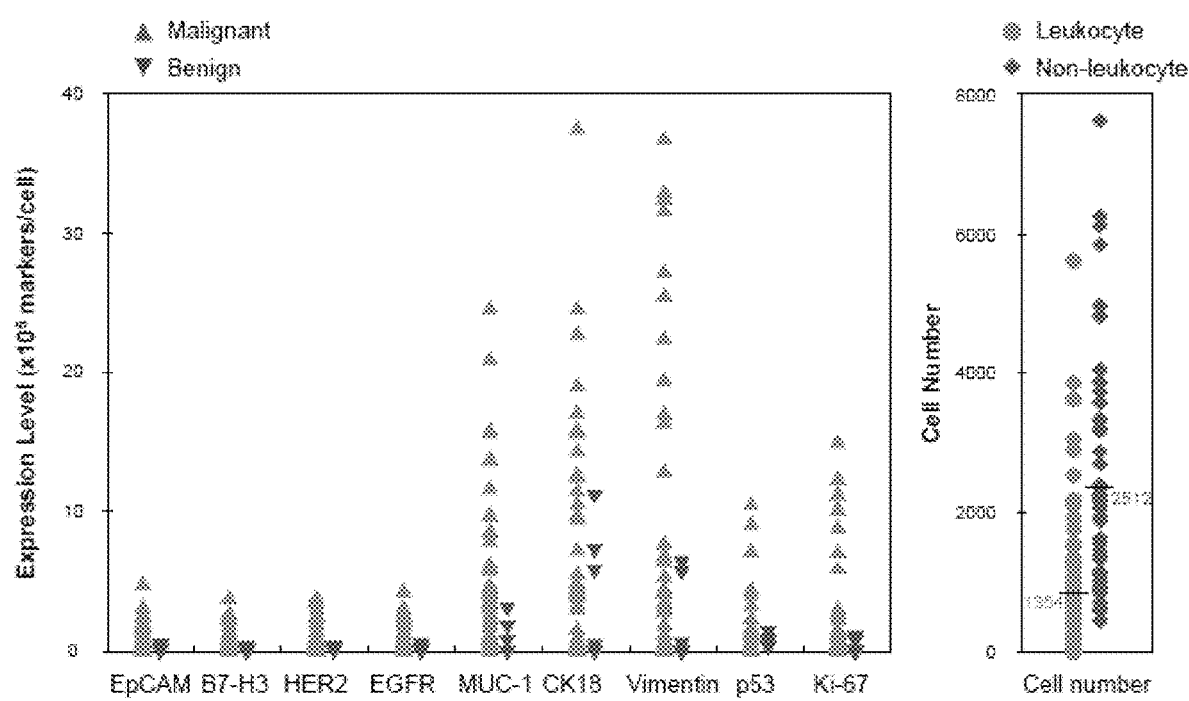
FIG. 6 is a dot plot showing the variability of marker levels stratified by diagnosis and by global leukocyte versus non-leukocyte comparisons. Left: Individual marker expression levels for both malignant and benign samples. Right: Overall leukocyte and non-leukocyte cell counts.

Example 2. Expression Levels of Cancer-Related Proteins were Heterogenous Across Epithelial Tumors To determine whether protein expression levels (shown in FIG. 3) correlated between samples, levels were plotted for each patient. The results showed that there was considerable heterogeneity in the magnitude of expression across patient samples (FIG. 4). To further examine the interrelationship between markers, Spearman correlations were calculated (FIG. 5). MUC-1, EGFR, B7-H3 and HER2 demonstrated moderate correlations with one another (coefficients ranging from 0.4-0.6). No strong associations were found between EpCAM expression and the other four extracellular markers. Intracellular and extracellular marker expressions did not correlate strongly with one another. FIG. 6 displays the distribution of individual markers per cell. With the exception of MUC-1, all extracellular markers displayed lower variability while intracellular makers generally showed higher variability. In the samples tested, no single marker was able to universally discriminate between malignant and benign samples.

Example 3. Clinical Performance of Cancer Markers

Figure 7A:
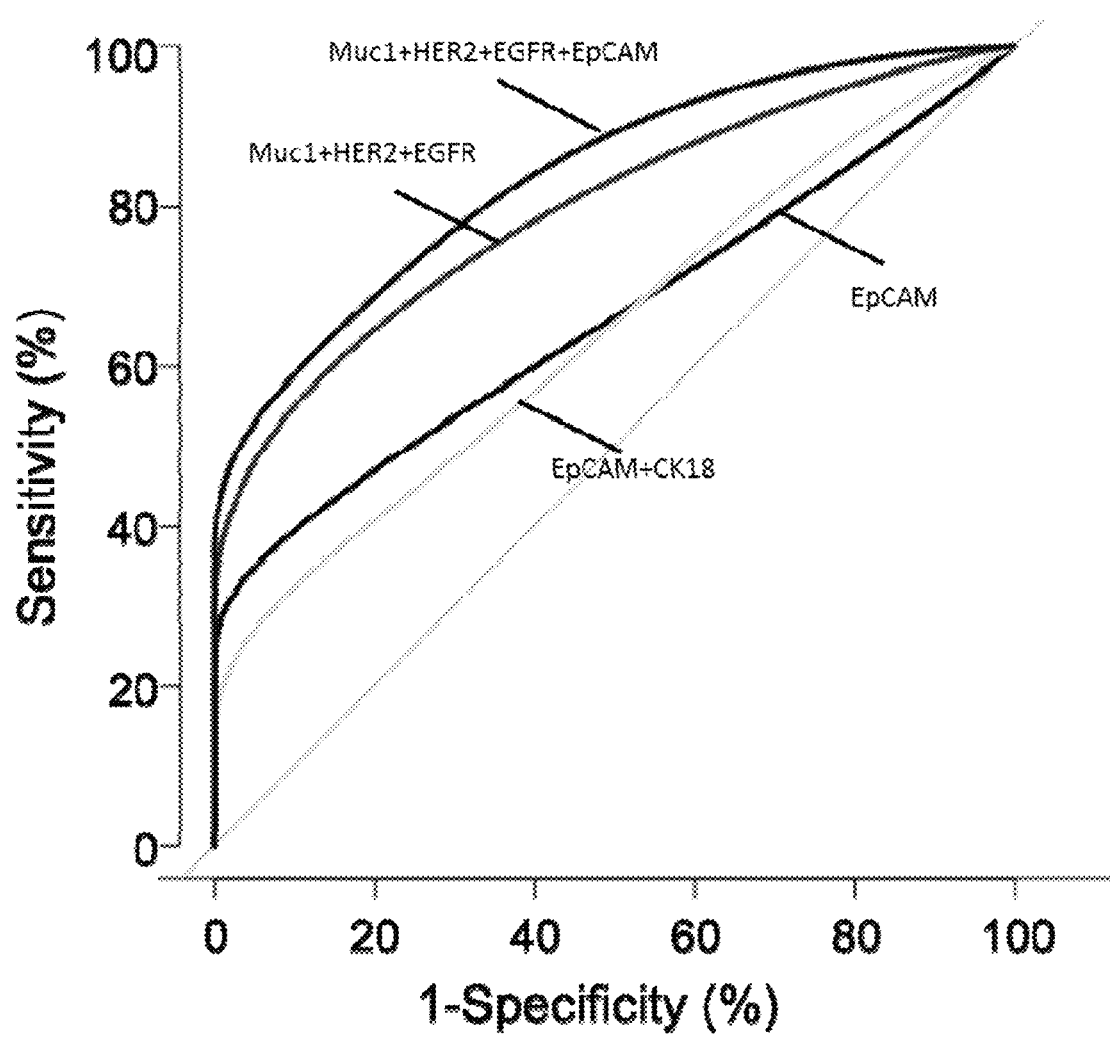
FIG. 7A is a graph showing receiver operating characteristic (ROC) curves for single markers, a dual marker set, as well as for triple and quadruple marker combinations to determine optimum DMR threshold values.

To determine the clinical performance of the nine cancer-related markers, receiver operating characteristic (ROC) analyses were performed. FIG. 7A compares the areas under the ROC curves ($A_z$ values) for individual markers, a dual marker pair (EpCAM+CK18), as well as for the best triple and quadruple marker combinations.

Next, a threshold was established for creating a classification rule based on a single marker or on the estimated risk score function of a marker combination. Optimized diagnostic marker combinations and their discriminatory values were then retrospectively analyzed for each patient sample (Table 2).

Among individual markers, MUC-1 displayed the highest area under the curve ($A_z$=0.82), closely followed by EGFR and HER2. Interestingly, EpCAM, a marker routinely used for circulating tumor cell (CTC) analysis and enrichment (S. L. Stott et al., Sci. Transl. Med. 2, 25ra23 (2010)), showed a lower $A_z$ (0.65). Even the combination of EpCAM and CK18 (the accepted criteria used to identify CTCs in peripheral blood) showed a low $A_z$ (0.66). Table 2 summarizes the diagnostic sensitivity, specificity and accuracy for each marker and combination of markers, along with their respective optimized µNMR threshold values for malignancy. The highest accuracy for this cohort was observed for a statistically weighted (see above) quadruple marker subset (MUC-1+EGFR+HER2+EpCAM; 96% accuracy); this was followed closely by weighted triple markers (MUC-1+EGFR+HER2; 92% accuracy). EpCAM and CK18 achieved an overall diagnostic accuracy of 80%, where a higher sensitivity (84%) was offset by low specificity (50%). The quadruple marker combination correctly diagnosed 48 out of 50 cases as either malignant or benign. Interestingly, both incorrect cases (patients 21 and 42) contained only core biopsy evidence of inflammation, marked by the presence of reactive fibrosis, histiocytes, and other inflammatory cells. It is well appreciated that when the same data set is used to generate a classification rule and to derive diagnostic accuracies the results may be overly optimistic. To reduce this potential bias, "leave-one out" cross-validation techniques were used to estimate prediction accuracies and used the bootstrap method to estimate the standard error for the accuracy estimate. Table 2 summarizes the 95% confidence intervals for marker combinations using this method and confirms their high accuracies. To eliminate any remaining bias, an independent patient test set was also employed.

TABLE 2

Ranges of sensitivity, specificity, and cross-validation obtained for all single markers and for specific marker combinations

| Number | Marker | DMR value | Sensitivity | Specificity | Accuracy | Cross Validation |
|---|---|---|---|---|---|---|
| Single | MUC-1 | 0.25 | 66% (51%-78%) | 83% (44%-97%) | 68% | 66% (48%-84%) |
|  | EGFR | 0.20 | 64% (49%-76%) | 83% (44%-97%) | 66% | 62% (42%-82%) |
|  | B7-H3 | 0.11 | 68% (53%-80%) | 67% (30%-90%) | 68% | 58% (39%-77%) |
|  | HER2 | 0.24 | 64% (49%-76%) | 100% (61%-100%) | 68% | 62% (48%-76%) |
|  | Ki-67 | 0.10 | 68% (53%-80%) | 67% (30%-90%) | 68% | 62% (37%-89%) |
|  | EpCAM | 0.21 | 59% (44%-72%) | 67% (30%-90%) | 60% | 46% (25%-67%) |
|  | Vimentin | 0.08 | 59% (44%-72%) | 67% (30%-90%) | 60% | 56% (31%-81%) |
|  | CK18 | 0.06 | 73% (58%-84%) | 50% (19%-81%) | 70% | 64% (36%-92%) |
|  | p53 | 0.38 | 41% (28%-56%) | 83% (44%-97%) | 46% | 40% (22%-58%) |
| Dual | EpCam + CK18 (unweighted) | 0.27 | 84% (71%-92%) | 50% (19%-81%) | 80% | 78% (43%-100%) |
| Triple | MUC-1 + HER2 + EGFR (weighted) | 1.23 | 95% (85%-99%) | 67% (30%-90%) | 92% | 86% (65%-100%) |
| Quad | MUC-1 + HER2 + EGFR + EpCAM (weighted) | 1.60 | 100% (92%-100%) | 67% (30%-90%) | 96% | 86% (63%-100%) |

To eliminate potential sources of error, data over-fitting, and to comply with recently published expert recommendations for proteomic biomarker studies (H. Mischak et al., Sci. Transl. Med. 2, 46ps42 (2010)), the 4-marker panel was tested in 20 additional patients (Table 1). μNMR was able to establish correct diagnoses for all 20 patients at an accuracy of 100% and at a 95% confidence interval of 83.2-100%.

TABLE 3

| Patient | DMR values | | | | | DMR diag-nosis | True diag-nosis |
|---|---|---|---|---|---|---|---|
| | MUC-1 | HER2 | EGFR | EpCAM | Quad | | |
| 51 | 0.17 | 0.00 | 0.19 | 0.02 | 0.37 | Benign | Benign |
| 52 | 0.00 | 0.00 | 0.00 | 0.00 | 0.00 | Benign | Benign |
| 53 | 0.00 | 0.09 | 0.01 | 0.06 | 0.16 | Benign | Benign |
| 54 | 1.35 | 0.89 | 4.38 | 1.83 | 8.44 | Malignant | Malignant |
| 55 | 8.03 | 0.49 | 0.89 | 2.86 | 12.27 | Malignant | Malignant |
| 56 | 0.55 | 0.33 | 0.24 | 0.31 | 1.43 | Benign | Benign |
| 57 | 8.28 | 0.00 | 0.60 | 1.83 | 10.71 | Malignant | Malignant |
| 58 | 0.21 | 0.73 | 0.00 | 1.11 | 2.05 | Malignant | Malignant |
| 59 | 2.57 | 0.67 | 1.10 | 2.37 | 6.70 | Malignant | Malignant |
| 60 | 1.10 | 0.23 | 0.59 | 0.51 | 2.43 | Malignant | Malignant |
| 61 | 7.62 | 1.34 | 1.19 | 5.28 | 15.43 | Malignant | Malignant |
| 62 | 1.47 | 0.00 | 0.98 | 1.05 | 3.50 | Malignant | Malignant |
| 63 | 5.08 | 0.27 | 5.15 | 5.91 | 16.42 | Malignant | Malignant |
| 64 | 1.35 | 0.89 | 3.38 | 0.00 | 5.61 | Malignant | Malignant |
| 65 | 2.52 | 0.99 | 0.69 | 1.13 | 5.32 | Malignant | Malignant |
| 66 | 0.85 | 0.97 | 0.27 | 0.02 | 2.11 | Malignant | Malignant |
| 67 | 0.00 | 0.29 | 0.86 | 0.60 | 1.74 | Malignant | Malignant |
| 68 | 2.96 | 1.97 | 0.00 | 1.01 | 5.94 | Malignant | Malignant |
| 69 | 0.46 | 0.21 | 0.06 | 0.06 | 0.80 | Benign | Benign |
| 70 | 0.00 | 0.65 | 0.00 | 0.65 | 1.30 | Benign | Benign |

Example 4. The Four BioMarkers are Useful in a Variety of Cancers

To determine whether the four biomarkers were useful in detecting cancer cells in blood, the levels of MUC1, HER2, EGFR and EpCAM were measured in samples in which cells from three cancer cell lines were spiked into whole blood (about 200 cells spiked into 7 ml of whole blood). PaCa-3 is a pancreatic cancer cell line; MDA-MB-231 is an estrogen-independent and highly metastatic human breast tumor; and A549 is a carcinomic human alveolar basal epithelial cell line. The blood cells were lysed, the cells were treated with the antibody-MNPs, and μNMR detection was performed as described. The samples were measured two ways: by detecting levels of each analyte individually, and simultaneously (all four antibody-MNPs were added to the same sample).

Figure 7B:
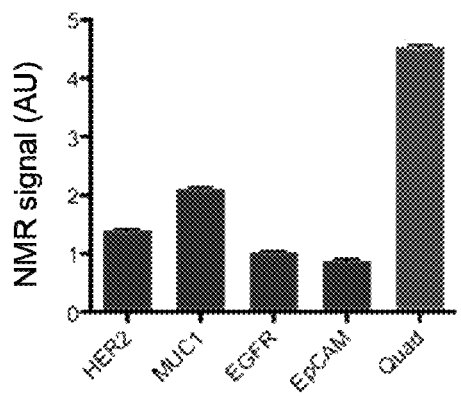
FIG. 7B is a set of three bar graphs showing levels of the four markers measured individually (HER2, MUC1, EGFR, and EpCAM) and simultaneously (Quad) in three different cell lines.
Figure 7B:
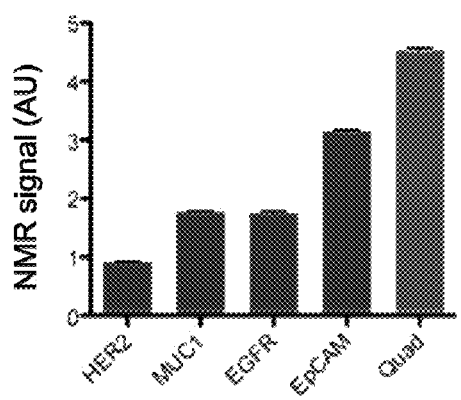
Figure 7B:
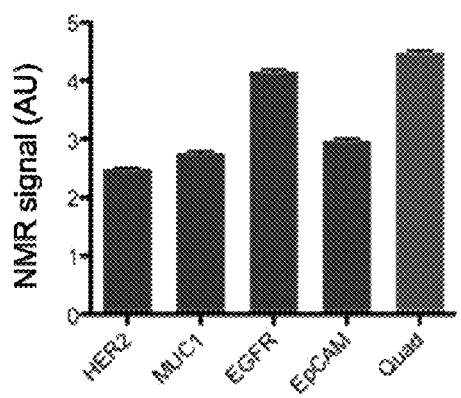

FIG. 7B shows that in three culture cancer cell lines, measuring all four markers ("QUAD") gave a similar result regardless of tumor origin, while the results from each individual marker varied greatly. While weighted averaging of the signal cannot be performed when the markers are measured simultaneously, as in other examples, this method significantly simplifies the assay procedure.

Example 5. Comparison to the Standard-of-Care

Figure 8:
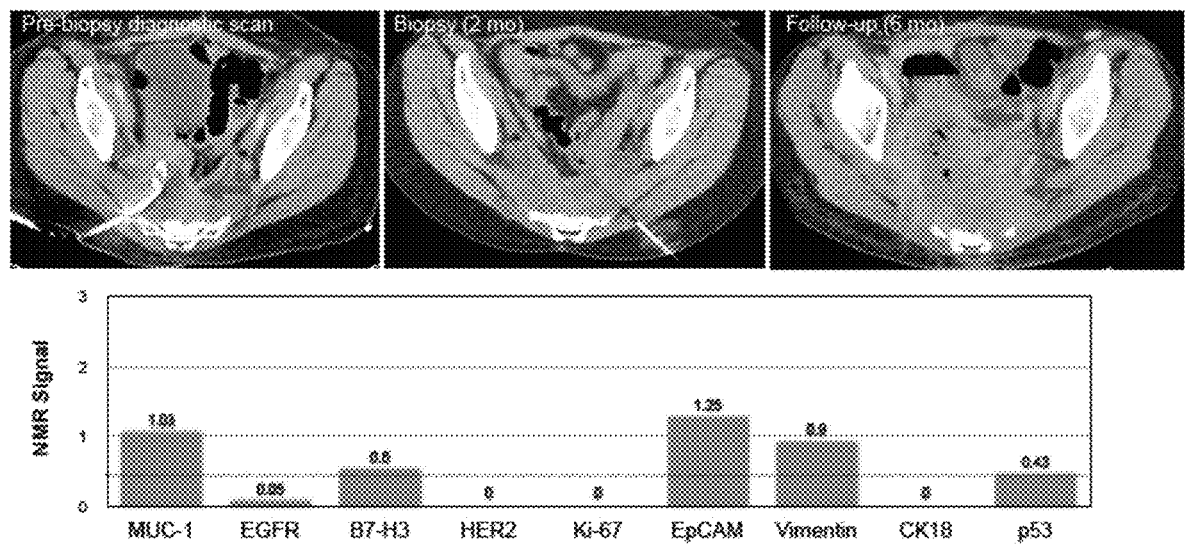
FIG. 8 shows images from a representative clinical case illustrating the potential role of μNMR for enhancing diagnostic accuracy and influencing management. Patient (3) underwent computed tomography (CT)-guided biopsy for an enlarging (2.5×6.8 cm) pre-sacral lesion in the setting of active metastatic rectal adenocarcinoma. Both cytology and core biopsy assessed the lesion as benign (inflammatory tissue). The lesion was thus treated with a drainage catheter. As shown in the graph, μNMR analysis, using the quadruple-marker combination (MUC-1+HER2+EGFR+EpCAM), unequivocally classified the lesion as malignant (μNMR value: 11.25; malignancy threshold ≥1.6). Repeat chest and abdomen CT after two months noted a significant interval enlargement of the biopsied lesion, as well as new metastases.

The mean clinical turnaround time for conventional pathology, from sample submission to final report, was 3 days for cytology (range 1-8 days) and 4 days for surgical pathology (range 1-11 days). The measurement time for μNMR was typically <60 minutes. Conventional cytology on FNA specimens was performed in 49 of 50 cases and was diagnostic in 36 of 49 cases (accuracy 74%; Table 4). Conventional histology was obtained on all cores and correctly diagnosed 45 cases (accuracy 84%; Table 3). The remaining results were either non-diagnostic (5 cases) or false negative (8 cases). Thus, μNMR performed consistently better (accuracy 96%; Table 3) than the current standard-of-care. FIG. 8 illustrates one case in which μNMR analyses were positive for malignancy, but conventional pathology (independent of radiographic or detailed clinical data) determined the samples as benign.

TABLE 4

The diagnostic accuracy of different techniques compared to the standard of care

| Technique | n | Diagnostic | Non-diagnostic | Misdiagnosis | Sensitivity | Specificity | Accuracy |
|---|---|---|---|---|---|---|---|
| Fine needle aspirate | 49 | 36 | 13 | 11 | 70% | 100% | 74% |
| Core biopsy | 50 | 45 | 5 | 8 | 82% | 100% | 84% |
| μNMR | 50 | 50 | 0 | 2 | 100% | 67% | 96% |

Example 6. Other Markers

A key determinant of cancer prognosis is the rate of tumor proliferation. In this study, the cell cycle marker Ki-67 was measured to gauge the proliferative index in malignant cells. The proliferate index was found to vary considerably (range: 0-100%) across all patients and across subgroups of patients with the same disease and at similar stages (e.g. colorectal cancer: proliferative index 1-100%; pancreatic ductal adenocarcinoma: proliferative index 3-75%). However, when patients were classified into treatment responders and non-responders, Ki-67 showed statistically significant differences between the groups (p=0.0087). The responders had a mean value of 6% proliferation (range: 0-13; standard error: 3.3) while the non-responders had a mean value of 23% (95% CI: 10-36; standard error: 6.3). Cancer associated leukocyte counts were also determined for each FNA sample. Whilst there was considerable variability across all samples (FIG. 6), non-responders showed significantly higher levels of leukocytes in FNA samples (37.5±25.4% vs. 28±20.7%). This finding is consistent with earlier reports that an inflammatory signature is indicative of worse prognosis (A. Saadi et al., Proc. Natl. Acad. Sci. U.S.A. 107, 2177 (2010); M. Cristofanilli et al., Cancer 110, 1436 (2007); N. Erez et al., Cancer Cell 17, 135 (2010)). Protein levels of p53 also showed a wide variability but were not found to differ significantly between responders and non-responders. Finally, vimentin was investigated as a cancer marker since this intermediate filament protein has been associated with epithelial mesenchymal transition (R. Kalluri and R. A. Weinberg, J. Clin. Invest. 119, 1420 (2009)), metastases (G. Lahat et al., PLoS One 5, e10105 (2010)) and therapy resistance (C. J. Creighton et al., Proc. Natl. Acad. Sci. U.S.A. 106, 13820 (2009)). In this study, vimentin was not found to add any further diagnostic information to that provided by other markers. Instead, vimentin levels appear to correlate with patient treatment history. Compared to their chemotherapy-naive counterparts, actively or pretreated malignant lesions expressed higher vimentin levels (mean 0.78±0.20 vs. 0.30±0.11; p=0.04).

Example 7. Variability and Sample Stability

Figure 9F:
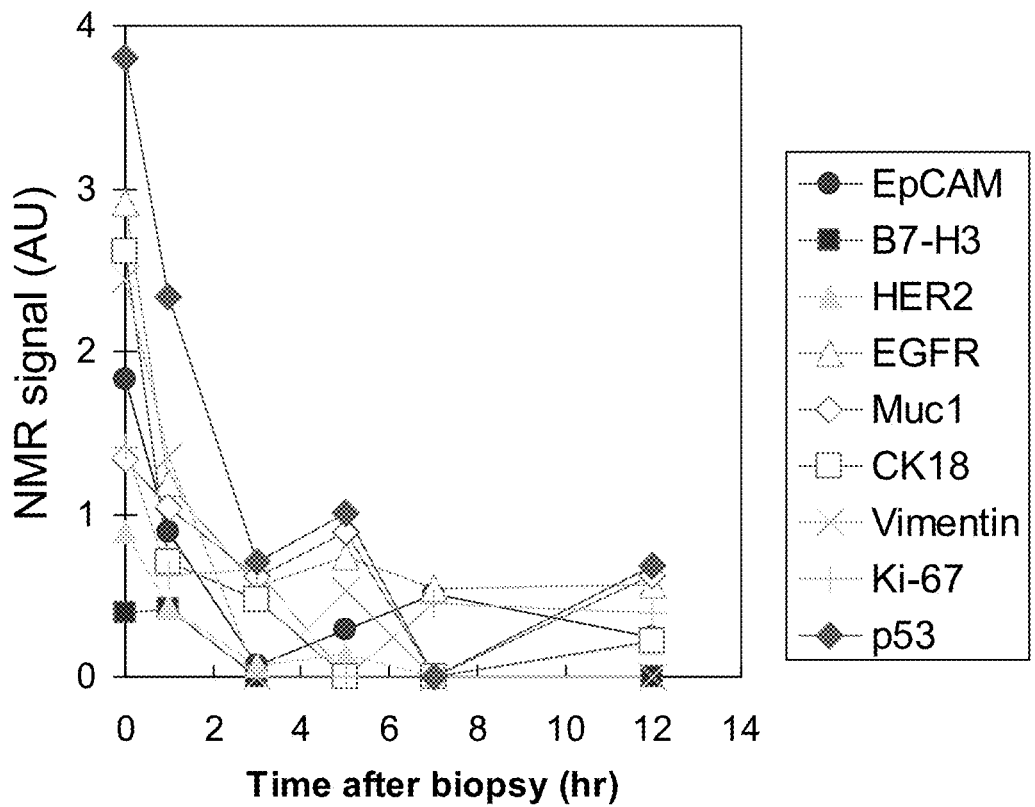
FIG. 9F shows the effect of time at 4° C. before fixation (e.g. during transport to central laboratory facility) on protein measurements. Note the rapid change in expression levels in unfixed samples. The typical half-life of markers is <2 hrs.
Figure 9G:
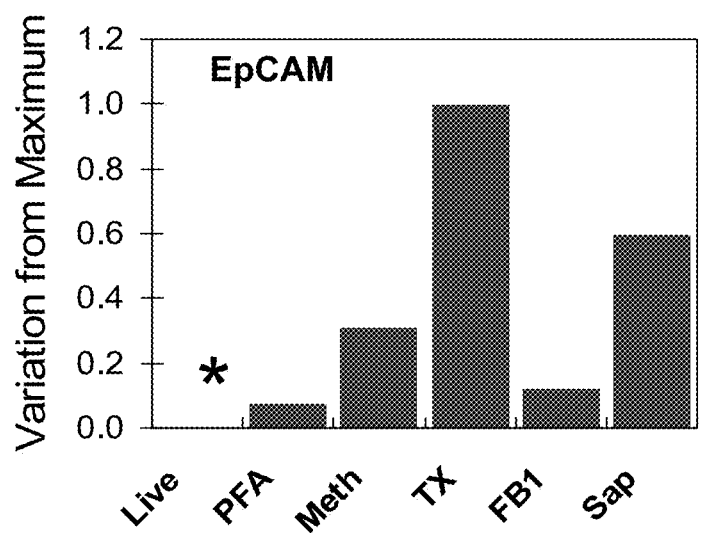
FIG. 9G shows the effect of various means of fixation. With 2% paraformaldehyde (PFA), cellular proteins could be preserved (>12 hrs) at the level comparable to that of live cells.

Clinicians regard data from a single pathological snapshot as proxies to the intrinsic biology of the tumor at the time of biopsy. However, when such information is used to make significant medical decisions, such as whether to initiate chemotherapy in the neoadjuvant setting (i.e., before surgery), data fidelity and reliability become paramount. It was therefore sought to identify the sources contributing to potential sample variability. The reproducibility of the μNMR measurements (n=30 samples) was initially determined, which confirmed that repeated measurements of each sample produced similar results (<0.6% variability overall and <0.3% for intracellular markers; FIG. 9A). This finding is remarkable for non-purified, blood-containing samples of cellular protein biomarkers. However, when different needle aspirates (n=13) were obtained along the identical coaxial needle pass, considerable heterogeneity was observed (FIG. 9B). Whilst for most extracellular markers, variation from the mean only reached a maximum of 30%, variation for intracellular markers such as p53 (FIG. 9B) was more pronounced. However, when additional samples were obtained from different regions of the same tumor, even extracellular markers showed mean variabilities of ~90% (FIG. 9C). Finally, it is important to note that clinical samples are often processed in central laboratories and spend variable amounts of time in transit and in refrigerators before batch processing. To determine how such treatment might affect protein measurements, sample aliquots were stored at 4° C. for various amounts of time prior to processing (FIG. 9F). Surprisingly, there was a considerable decrease in marker expression over time, with a mean loss of approximately 100% within the first hour after sampling. After 3 hours, marker loss appeared to plateau, when marker expression was down by about 400%. These changes likely reflect differences in protein half-lives as well as degradation by proteases and/or pH drifts in the samples. Treating the samples with 2% paraformaldehyde (PFA) preserved cellular proteins at the level comparable to that of live cells for at least 12 hours (FIG. 9G).

REFERENCES

1. R. C. J. Bast et al., *Clin. Cancer Res.* 11, 6103 (2005).
2. K. L. Bolton et al., *Cancer Epidemiol. Biomarkers Prev.* 19, 992 (2010).
3. R. G. Sheiman et al., *Am. J. Roentgenol.* 170, 1603 (1998).
4. P. R. Mueller and E. vanSonnenberg, *N. Engl. J. Med.* 322, 1364 (1990).
5. J. Y. Pierga et al., *Clin. Cancer Res.* 14, 7004 (2008).
6. J. Kaiser, *Science* 327, 1072 (2010).
7. S. Hanash and A. Taguchi, *Nat. Rev. Cancer* 10, 652 (2010).
8. T. D'Alfonso et al., *Am. J. Surg. Pathol.* 34, 575 (2010).
9. A. Khan et al., *Ann. Surg. Oncol.* 12, 697 (2005).
10. A. Makris et al., *Breast Cancer Res. Treat.* 53, 51 (1999).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating an intra-abdominal tumor in a subject, the method comprising:
    obtaining a sample from the subject, wherein the sample is not from breast or lung tissue;
    detecting levels of biomarkers consisting of MUC-1, HER2, EGFR, and EpCAM in the sample by contacting the sample with antibodies or antigen-binding fragments thereof that bind to MUC-1, HER2, EGFR, and EpCAM and are labeled with superparamagnetic cross-linked iron oxide (CLIO) nanoparticles having a hydrodynamic diameter of 28.8 nm;
    comparing the levels of MUC-1, HER2, EGFR, and EpCAM in the sample to reference levels; and
    administering a treatment for cancer to a subject who has levels of MUC-1, HER2, EGFR, and EpCAM above the reference levels.

2. The method of claim 1, wherein a single undivided sample is contacted with a mixture of antibodies, or antigen-binding fragments thereof, that bind to MUC-1, HER2, EGFR, and EpCAM, simultaneously.

3. The method of claim 1, wherein the sample is subdivided into at least four subparts, and each antibody, or antigen-binding fragment thereof, that binds to MUC-1, HER2, EGFR, or EpCAM is contacted with a single subpart.

4. The method of claim 1, wherein the levels of MUC-1, HER2, EGFR, and EpCAM are detected using diagnostic magnetic resonance (DMR) or direct magnetic detection.

5. The method of claim 1, wherein the sample comprises blood or a subfraction thereof.

6. The method of claim 1, wherein the sample comprises a biopsy sample.

7. The method of claim 6, wherein the biopsy sample is a fine needle aspirate (FNA), endoscopic biopsy, or core needle biopsy.

8. The method of claim 1, wherein the sample comprises cells from the pancreas, prostate, kidney, stomach, esophagus, bladder, endometrial, cervix, biliary, thyroid, ovary or colon of the subject.

9. The method of claim 1, wherein the intra-abdominal tumor is from a pancreas, prostate, kidney, stomach, esophagus, bladder, endometrial, cervix, biliary, thyroid ovary or colon tumor.

10. The method of claim 1, wherein the treatment for cancer comprises one or more of surgical treatment, chemotherapy, immunotherapy, and/or radiotherapy.

11. The method of claim 1, wherein the antibodies or antigen-binding fragments thereof are linked to the CLIO nanoparticles via transcyclooctene (TCO)/tetrazine (Tz) chemistry.

* * * * *

UNITED STATES PATENT AND TRADEMARK OFFICE
CERTIFICATE OF CORRECTION

PATENT NO. : 10,712,343 B2
APPLICATION NO. : 15/401806
DATED : July 14, 2020
INVENTOR(S) : Weissleder et al.

Page 1 of 1

It is certified that error appears in the above-identified patent and that said Letters Patent is hereby corrected as shown below:

In the Claims

In Column 26, Line 54 (approx.), Claim 9, after "thyroid" insert -- , --

Signed and Sealed this
Thirteenth Day of October, 2020

Andrei Iancu
*Director of the United States Patent and Trademark Office*